(12) United States Patent
Kol et al.

(10) Patent No.: US 6,333,423 B1
(45) Date of Patent: Dec. 25, 2001

(54) ULTRA-HIGH ACTIVITY NON-METALLOCENE PRE-CATALYST AND METHOD FOR CATALYTIC POLYMERIZATION OF ALPHA-OLEFIN MONOMERS

(75) Inventors: Moshe Kol, Ramat Gan; Edit Tshuva, Rechovot; Zeev Goldschmidt, Petach-Tikva, all of (IL)

(73) Assignees: Ramot University Authority for Applied Research and Industrial Development Ltd., Ramat Gan; Bar-Ilan University, Tel Aviv, both of (IL)

( * ) Notice: Subject to any disclaimer, the term of this patent is extended or adjusted under 35 U.S.C. 154(b) by 0 days.

(21) Appl. No.: 09/394,280

(22) Filed: Sep. 10, 1999

(51) Int. Cl.⁷ .................................. C07F 7/00; C07F 7/28
(52) U.S. Cl. .................. 556/56; 556/54; 556/13; 556/19; 502/150; 526/172
(58) Field of Search .......................................... 556/54, 56

(56) References Cited

PUBLICATIONS

Hinshaw et al., Inorganic Chemistry vol. 28, No. 25, pp. 4483–4491, 1989.*

Hirotsu et al., Bull. Chem. Soc. Jpn. vol. 70, pp. 649–657, 1997.*

\* cited by examiner

Primary Examiner—David W. Wu
Assistant Examiner—R. Rabago

(57) ABSTRACT

Disclosed are compounds of the following formulae, and their use in the polymerization of olefins:

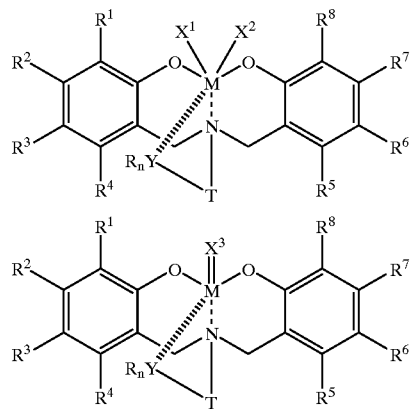

wherein M is preferably titanium, zirconium or hafnium, $R^1$–$R^8$ are univalent radicals, $X^1$ and $X^2$ are univalent ligands, $X^3$ is a divalent ligand, and ($R_nY$—T) is an optional donor or non-donor group.

36 Claims, 2 Drawing Sheets

ULTRA-HIGH ACTIVITY NON-METALLOCENE PRE-CATALYST AND METHOD FOR CATALYTIC POLYMERIZATION OF ALPHA-OLEFIN MONOMERS

FIELD AND BACKGROUND OF THE INVENTION

The present invention relates to catalytic polymerization of alpha-olefins, and more particularly, to an ultra-high activity non-metallocene pre-catalyst featuring an amine bis(phenolate) ligand-metal chelate and a method for catalytic polymerization of alpha-olefin monomers using this pre-catalyst.

Currently, there is significant interest relating to methods and systems of catalytic polymerization of alpha-olefin monomers based on a 'pre-catalyst' featuring a metal bound to one or more spectator ligands, where the pre-catalyst may be soluble in a liquid phase solvent, or is adsorbed on a solid surface, and where alpha-olefin monomer reactant may be liquid or gas phase. In such methods and systems, typically, the pre-catalyst is activated by at least one 'co-catalyst', where the combination of the activated pre-catalyst and the at least one co-catalyst functions as a single chemical entity, or complex 'catalyst', for polymerization of the alpha-olefin monomer. The field of catalytic polymerization of alpha-olefin monomers is of significant industrial importance, as more than 50 million tons of poly(alpha-olefin) products, such as polyetheylenes and polypropylenes, are produced each year, involving metal based catalytic processes and systems.

Hereinafter, the term 'pre-catalyst' refers to a chemical entity, in general, and to a chemical compound, in particular, which, when activated by at least one 'co-catalyst', becomes part of a 'catalyst' functional for catalytic polymerization of an alpha-olefin monomer, under proper polymerization reaction conditions. Without the presence of at least one co-catalyst, a pre-catalyst is ineffective for catalytic polymerization of an alpha-olefin monomer, and consequently exhibits essentially no catalytic activity for polymerization of an alpha-olefin monomer. Here, when referring to catalytic activity during a polymerization reaction, reference is with respect to the catalytic activity of a pre-catalyst, and it is to be understood that the pre-catalyst is functioning in concert with at least one co-catalyst for effecting catalytic polymerization of an alpha-olefin monomer. Thus, the present invention focuses on a new and novel pre-catalyst compared to pre-catalysts currently used for catalytic polymerization of alpha-olefin monomers.

Currently, one of the major goals in this field is to produce a variety of new types of poly(alpha-olefin) products, for example, polymers made from alpha-olefin monomers featuring more than three carbon atoms such as 1-hexene, having well defined physicochemical properties and characteristics, such as mechanical strength, elasticity, melting point, and chemical resistance, applicable for manufacturing a diversity of end products. This may be achieved by polymerizing different types of alpha-olefin monomers, in order to produce a variety of homo-polymers and co-polymers, with varying degrees of monomer incorporation.

Typically, degree of monomer incorporation strongly depends upon catalyst activity for polymerization of a given alpha-olefin monomer. Recently, Britovsek, G. J. P., et al., in "The Search For New-Generation Olefin Polymerization Catalysts: Life Beyond Metallocenes", *Angew. Chem. Int. Ed. Engl.* 38, 428–447, 1999, provided a practical quantitative ranking of catalytic activity, with respect to weight of a pre-catalyst, (grams polymer produced)/(mmole-pre-cat. hr), for ethylene polymerization, under one bar pressure, as follows: very low<1, low 1–10, moderate 10–100, high 100–1000, very high>1000. Their ranking is derived from data of catalytic polymerization of ethylene, which is the easiest alpha-olefin monomer to polymerize. Catalytic activity for polymerization of other larger alpha-olefin monomers, such as 1-hexene and 1-octene, is usually at least one order of magnitude less. Thus, a pre-catalyst for polymerization of 1-hexene, for example, may be considered exhibiting high, and very high, activity in the range of about 10–100, and 100–1000, grams/(mmole-pre-cat. hr), respectively.

Physicochemical properties of polymers include, are directly related to, and are controllable by, polymer molecular weight and molecular weight distribution. These values are highly relevant with respect to producing different types of polymers. For example, ultra-high molecular weight polyethylene (UHMWPE), having an average molecular weight above 3,000,000 has the highest abrasion resistance of thermoplastics and a low coefficient of friction. Unlike synthesis of small molecules, however, polymerization reactions involve random events characterized by formation of polymers having a range of molecular weights, rather than a single molecular weight. Typically, polymers are better defined and characterized in relation to narrow molecular weight ranges.

The accepted parameter for defining polymer molecular weight distribution is the polydispersity index (PDI), which is the weight average molecular weight, $M_w$, divided by the number average molecular weight, $M_n$, or, $M_w/M_n$. Depending upon the actual application, ideally, a catalytic polymerization system features 'living' polymerization in which the rate of initiation is higher than the rate of propagation leading to a PDI of close to 1, and involving a single catalytic active site. This has been achieved in very few systems for catalytic polymerization of alpha-olefin monomers. A PDI of 2.0, signifying 'non-living' polymerization, is often found in metallocene catalytic systems, also involving a single catalytic active site. Classical heterogeneous Ziegler-Natta catalytic systems usually lead to a broader range of molecular weights with a PDI of about 5. One current challenge is to design alpha-olefin polymerization pre-catalysts, and catalytic systems including such pre-catalysts, leading to poly(alpha-olefin) products with low values of PDI.

Metallocene pre-catalysts, featuring a metal complex including a metal atom, for example from Group IV transition elements such as titanium, zirconium, and hafnium, bound to two ligands from the well known cyclopentadienyl (Cp) family of ligands such as pentamethylcyclopentadienyl, indenyl, or fluorenyl, were introduced during the last two decades for the purpose of catalytic polymerization of alpha-olefin monomers. The most common type of metallocene pre-catalyst is a neutral complex including a metal in oxidation state of +4, bound to two anionic ligands in addition to two standard Cp ligands, for example, bis(cyclopentadienyl)titanium dichloride, also known as titanocene dichloride. A related group of complexes is 'constrained geometry' pre-catalysts, featuring a metal bound to both a single Cp type ligand and a second anionic group, where the Cp ligand and second anionic group are covalently linked.

Using metallocene and metallocene type pre-catalysts in catalytic processes and systems for polymerization of alpha-olefin monomers affords better control of molecular weight and narrower molecular weight distribution, translating to lower values of PDI, relative to the classical Ziegler-Natta family of pre-catalysts such as titanium trichloride using a trialkyl-aluminum co-catalyst. Metallocene and metallocene type pre-catalysts, processes, and systems are well known and taught about in the art. These pre-catalysts, processes and systems are, however, limited in many respects relating to the above discussion.

Foremost, with respect to catalytic activity, metallocene type pre-catalysts typically exhibit relatively moderate activity for polymerizing a small variety of alpha-olefin monomers. With respect to poly(alpha-olefin) product types and variety, alpha-olefin monomers polymerized by metallocene pre-catalysts are mostly short chain ethylene and propylene, which are already well taught about. Metallocene pre-catalysts are limited in terms of availability and versatility. With respect to pre-catalyst availability, metallocene type pre-catalysts are relatively difficult to synthesize, a fact which affects the possibility of developing new varieties of metallocene type alpha-olefin polymerization pre-catalysts.

Due to continued searching for new poly(alpha-olefin) products exhibiting selected well defined physicochemical properties and characteristics, combined with the above limitations associated with metallocene pre-catalysts, there is growing interest in developing non-metallocene alpha-olefin polymerization pre-catalysts, and related catalytic processes, and systems. The main emphasis is on obtaining new alpha-olefin polymerization pre-catalysts exhibiting higher activity, stability, and availability needed for enabling better control over industrially important polymer parameters such as molecular weight, molecular weight distribution, product type, and variety.

The first step towards development of non-metallocene pre-catalysts was taken by the introduction of a 'half sandwich' pre-catalyst, featuring a complex including a Cp type ligand bridging to a heteroatom donor. An example of such a pre-catalyst is a phenolate constrained geometry polymerization pre-catalyst disclosed in U.S. Pat. No. 5,856,258. The pre-catalyst described therein shows relatively high activity of about 1,300 grams/(mmole-pre-cat. hr) for polymerization of alpha-olefin monomers, however monomers polymerized are limited to ethylene, propylene, and styrene.

A non-metallocene alpha-olefin polymerization catalytic system is disclosed in U.S. Pat. No. 5,852,146, and features a bis(hydroxy aromatic nitrogen ligand) transition metal pre-catalyst, functioning with an activating methylaminoxane (MAO) co-catalyst. Relatively high catalytic activity of about 4,000 grams/(mmole-pre-cat. hr) is reported for polymerization of ethylene only. Moreover, MAO is needed in large quantities as co-catalyst, which, in general poses notable limitations relating to cost and containment. MAO used in large quantities is costly, and needs to be properly disposed of with regard to environmental considerations.

Living polymerization of 1-hexene is recently described by Schrock, R. R., in *J. Am. Chem. Soc.* 119, 3830, 1997, and is disclosed in U.S. Pat. No. 5,889,128. One of the non-metallocene pre-catalyst compositions described therein comprises a dimethyl complex in which the metal atom is chelated to a tridentate spectator ligand, which is activated by a non-MAO boron salt co-catalyst. Catalytic activity under the conditions described was considered high, of about 200 grams/(mmole-pre-cat. hr), and the molecular weight of the obtained poly(1-hexene) product is moderate, of about 50,000 grams/mole.

Living polymerization of 1-hexene is also described by McConville, D. H., in *J. Am. Chem. Soc.* 118, 10008, 1996.

They describe a moderately active non-metallocene polymerization pre-catalyst, exhibiting activity of about 40 g/(mmole-pre-cat. hr), involving activation of a pre-catalyst featuring a dimethyl metal complex of a bis(amide) ligand, with a non-MAO boron Lewis acid as co-catalyst under room temperature, for producing a moderate molecular weight polymer, of molecular weight of 40,000 grams/mole. The same pre-catalyst, but functioning with MAO as co-catalyst in large excess, under the same reaction conditions, yields significantly higher activity, as reported by McConville, D. H., in *Macromolecules* V. 29, 5241, 1996. Again, limitations associated with using MAO as co-catalyst are present.

Another active non-metallocene living 1-hexene polymerization pre-catalyst functioning with a non-MAO co-catalyst, is reported by Kim, K., in *Organometallics* 17, 3161, 1998. The described catalyst system exhibits activity of about 400 gramsl(mmole-pre-cat. hr).

A non-metallocene non-living 1-hexene polymerization pre-catalyst is disclosed in U.S. Pat. No. 5,807,801. The pre-catalyst exhibits high activity, of on the order of $10^6$ g/(mmole-pre-cat. hr), when the pre-catalyst is, again, activated with MAO as co-catalyst, for the polymerization process taking place at 50° C.

A non-metallocene bis(phenolate) pre-catalyst is reported by Schaverien, C. J., in *J. Am. Chem. Soc.* 117 3008, 1995. The pre-catalyst described exhibits limited activity, of about 10 g/(mmole-pre-cat. hr), for tactic polymerization of 1-hexene, yielding high molecular weight isotactic poly(1-hexene).

In view of the above discussed limitations, to one of ordinary skill in the art, there is thus a need for, and it would be advantageous to have an ultra-high activity non-metallocene pre-catalyst and corresponding method for catalytic polymerization of alpha-olefin monomers, not limited to activation by large quantities of a co-catalyst such as MAO, and also characterized by high stability, readily obtained or synthesized, and capable of producing different types and varieties of poly(alpha-olefin) products having high molecular weight, and low molecular weight distribution. Moreover, there is a need of such a pre-catalyst and method for producing alpha-olefin polymers other than polyethylenes and polypropylenes, having industrially applicable properties and characteristics.

SUMMARY OF THE INVENTION

The present invention relates to catalytic polymerization of alpha-olefin monomers using an ultra-high activity non-metallocene pre-catalyst featuring an amine bis(phenolate) ligand-metal chelate and a corresponding method.

It is therefore an object of the present invention to provide general structures and general formulas of an ultra-high activity non-metallocene pre-catalyst for catalytic polymerization of alpha-olefin monomers, wherein the pre-catalyst is an amine bis(phenolate) ligand-metal chelate.

It is a further object of the present invention to provide general structures and general formulas of an ultra-high activity non-metallocene pre-catalyst for catalytic polymerization of alpha-olefin monomers, wherein the precatalyst is an amine bis(phenolate) ligand-metal chelate featuring variability of the metal atom, ligands, aromatic groups, aromatic group substituents, a bridging group, and bridging group substituents including optional non-donor and donor groups.

It is another object of the present invention to provide a method for catalytic polymerization of alpha-olefin monomers featuring the use of an ultra-high activity non-metallocene pre-catalyst.

It is a further object of the present invention to provide a method for catalytic polymerization of alpha-olefin monomers featuring the use of an ultra-high activity non-metallocene pre-catalyst, wherein the pre-catalyst is an amine bis(phenolate) ligand-metal chelate.

It is a further object of the present invention to provide a method for catalytic polymerization of alpha-olefin monomers featuring the use of an ultra-high activity non-metallocene pre-catalyst, wherein the pre-catalyst is an amine bis(phenolate) ligand-metal chelate featuring variability of the metal atom, ligands, aromatic groups, aromatic group substituents, a bridging group, and bridging group substituents including optional non-donor and donor groups.

Thus, according to the present invention, there is provided a compound having a general structure selected from the group consisting of:

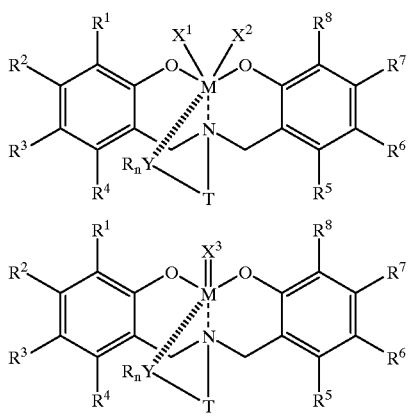

wherein: a solid line represents a covalent bond; a dashed line represents a bond having a varying degree of covalency and a varying degree of coordination; M is a metal atom covalently bonded to each O atom and bonded with varying degrees of covalency and coordination to the N atom; $X^1$ and $X^2$ are each a univalent anionic ligand covalently bonded to the metal atom; $X^3$ is a single divalent anionic ligand covalently bonded to the metal atom; $R^1$ through $R^4$ are each a univalent radical covalently bonded to first ($C_6$) aromatic group; $R^5$ through $R^8$ are each a univalent radical covalently bonded to second ($C_6$) aromatic group; and $(R_nY—T)$ is an optional group selected from the group consisting of a non-donor group covalently bonded to the N atom, wherein the non-donor group, T is a covalent bridging group between the N atom and Y, the Y is a group covalently bonded to the T, and, each of at least one $R_n$ is selected from the group consisting of a saturated substituent covalently bonded to the Y, an unsaturated substituent covalently bonded to the Y, and a univalent radical covalently bonded to the Y, and a donor group covalently bonded to the N atom, wherein the donor group, T is a covalent bridging group between the N atom and Y, the Y is a heteroatom covalently bonded to the T and bonded with varying degrees of covalency and coordination to the metal atom, and, optional $R_n$ substituents are selected from the group consisting of at least one saturated substituent covalently bonded to the Y, and at least one unsaturated substituent covalently bonded to the Y.

According to further features in preferred embodiments of the general structure of the compound described below, the metal atom is a transition metal atom.

According to further features in preferred embodiments of the general structure of the compound described below, the transition metal atom is selected from the group consisting of zirconium, hafnium and titanium.

According to further features in preferred embodiments of the general structure of the compound described below, the $X^1$ and the $X^2$ are each selected from the group consisting of a halide, a hydride, a saturated hydrocarbyl, an unsaturated hydrocarbyl, an alkoxide, an aryloxide, an dialkylamide, and an arylamide.

According to further features in preferred embodiments of the general structure of the compound described below, the $X^3$ is selected from the group consisting of a cyclometallated hydrocarbyl, and a radical, the radical including an alkylidene.

According to further features in preferred embodiments of the general structure of the compound described below, each of the $R^1$ through $R^4$ is selected from the group consisting of a hydrogen radical, a hydrocarbyl radical, and an alkoxide radical.

According to further features in preferred embodiments of the general structure of the compound described below, each of the $R^5$ through $R^8$ is selected from the group consisting of a hydrogen radical, a hydrocarbyl radical, and an alkoxide radical.

According to further features in preferred embodiments of the general structure of the compound described below, including the $(R_nY—T)$ group as the non-donor group, the T is a covalent bridging group selected from the group consisting of a saturated hydrocarbyl, and an unsaturated hydrocarbyl.

According to further features in preferred embodiments of the general structure of the compound described below, including the $(R_nY—T)$ group as the non-donor group, the Y is selected from the group consisting of a satura ted hydrocarbyl, and an unsaturated hydrocarbyl.

According to further features in preferred embodiments of the general structure of the compound described below, including the $(R_nY—T)$ group as the non-donor group, each of the at least one $R_n$ is a the saturated substituent selected from the group consisting of a methyl substituent and an ethyl substituent.

According to further features in preferred embodiments of the general structure of the compound described below, including the $(R_nY—T)$ group as the non-donor group, each of the at least one $R_n$ is a the univalent radical selected from the group consisting of a hydrogen radical and a methyl radical.

According to further features in preferred embodiments of the general structure of the compound described below, including the $(R_nY—T)$ group as the donor group, the T is a covalent bridging group selected from the group consisting of a saturated hydrocarbyl, an unsaturated hydrocarbyl, and a part of an aromatic system.

According to further features in preferred embodiments of the general structure of the compound described below, the saturated hydrocarbyl is selected from the group consisting of a methyl group and an ethyl group.

According to further features in preferred embodiments of the general structure of the compound described below, the unsaturated hydrocarbyl is an ethylene group.

According to further features in preferred embodiments of the general structure of the compound described below, the aromatic system is a pyridine ring.

According to further features in preferred embodiments of the general structure of the compound described below, including the $(R_nY—T)$ group as the donor group, the Y is a heteroatom selected from the group consisting of nitrogen, oxygen, sulfur, and phosphorous.

According to further features in preferred embodiments of the general structure of the compound described below, including the ($R_nY$—T) group as the donor group, the optional $R_n$ substituents are the at least one saturated substituent selected from the group consisting of a methyl substituent and an ethyl substituent.

According to further features in preferred embodiments of the general structure of the compound described below, including the ($R_nY$—T) group as the donor group, the optional $R_n$ substituents are the at least one unsaturated substituent, the unsaturated substituent includes a part of an aromatic system.

According to further features in preferred embodiments of the general structure of the compound described below, the compound is used as part of a catalyst for catalytic polymerization of an alpha-olefin monomer.

According to further features in preferred embodiments of the general structure of the compound described below, the compound is used as a pre-catalyst activated by a co-catalyst for catalytic polymerization of an alpha-olefin monomer.

According to another aspect of the present invention, there is provided a compound of a general formula selected from the group consisting of: $[\{(O)^1R^1R^2R^3R^4(C_6)^1(CH_2)^1(R_nY-T)N(CH_2)^2(C_6)^2R^5R^6R^7R^8(O)^2\}MX^1X_2]$ and $[\{(O)^1R^1R^2R^3R^4(C_6)^1(CH_2)^1(R_nY-T)N(CH_2)^2(C_6)^2(C_6)^2R^5R^6R^7R^8(O)^2\}MX^3]$, wherein: M is a metal atom covalently bonded to each the $(O)^1$ atom and bonded with varying degrees of covalency and coordination to the N atom; $X^1$ and $X^2$ are each a univalent anionic ligand covalently bonded to the metal atom; $X^3$ is a single divalent anionic ligand covalently bonded to the metal atom; $(C_6)^1$ is a six carbon aromatic group covalently bonded to $(O)^1$ and covalently bonded to $(CH_2)^1$; $R^1$ through $R^4$ are each a univalent radical covalently bonded to the $(C_6)^1$ group; $(C_6)^2$ is a six carbon aromatic group covalently bonded to $(O)^2$ and covalently bonded to $(CH_2)^2$; $R^5$ through $R^8$ are each a univalent radical covalently bonded to the $(C_6)^2$ group; and ($R_nY$—T) is an optional group selected from the group consisting of a non-donor group covalently bonded to the N atom, wherein the non-donor group, T is a covalent bridging group between the N atom and Y, the Y is a group covalently bonded to the T, and, each of at least one $R_n$ is selected from the group consisting of a saturated substituent covalently bonded to the Y, an unsaturated substituent covalently bonded to the Y, and a univalent radical covalently bonded to the Y, and a donor group covalently bonded to the N atom, wherein the donor group, T is a covalent bridging group between the N atom and Y, the Y is a heteroatom covalently bonded to the T and bonded with varying degrees of covalency and coordination to the metal atom, and, optional $R_n$ substituents are selected from the group consisting of at least one saturated substituent covalently bonded to the Y, and at least one unsaturated substituent covalently bonded to the Y.

According to further features in preferred embodiments of the general formula of the compound described below, the metal atom is a transition metal atom.

According to further features in preferred embodiments of the general formula of the compound described below, the transition metal atom is selected from the group consisting of zirconium, hafnium and titanium.

According to further features in preferred embodiments of the general formula of the compound described below, the $X^1$ and the $X^2$ are each selected from the group consisting of a halide, a hydride, a saturated hydrocarbyl, an unsaturated hydrocarbyl, an alkoxide, an aryloxide, an dialkylamide, and an arylamide.

According to further features in preferred embodiments of the general formula of the compound described below, the $X^3$ is selected from the group consisting of a cyclometallated hydrocarbyl, and a radical, the radical including an alkylidene.

According to further features in preferred embodiments of the general formula of the compound described below, each of the $R^1$ through $R^4$ is selected from the group consisting of a hydrogen radical, a hydrocarbyl radical, and an alkoxide radical.

According to further features in preferred embodiments of the general formula of the compound described below, each of the $R^5$ through $R^8$ is selected from the group consisting of a hydrogen radical, a hydrocarbyl radical, and an alkoxide radical.

According to further features in preferred embodiments of the general formula of the compound described below, including the ($R_nY$—T) group as the non-donor group, the T is the covalent bridging group selected from the group consisting of a saturated hydrocarbyl, and an unsaturated hydrocarbyl.

According to further features in preferred embodiments of the general formula of the compound described below, including the ($R_nY$—T) group as the non-donor group, the Y is selected from the group consisting of a saturated hydrocarbyl, and an unsaturated hydrocarbyl.

According to further features in preferred embodiments of the general formula of the compound described below, including the ($R_nY$—T) group as the non-donor group, each of the at least one $R_n$ is a the saturated substituent selected from the group consisting of a methyl substituent and an ethyl substituent.

According to further features in preferred embodiments of the general formula of the compound described below, including the ($R_nY$—T) group as the non-donor group, each of the at least one $R_n$ is a the univalent radical selected from the group consisting of a hydrogen radical and a methyl radical.

According to further features in preferred embodiments of the general formula of the compound described below, including the ($R_nY$—T) group as the donor group, the T is a covalent bridging group selected from the group consisting of a saturated hydrocarbyl, an unsaturated hydrocarbyl, and a part of an aromatic system.

According to further features in preferred embodiments of the general formula of the compound described below, the saturated hydrocarbyl is selected from the group consisting of a methyl group and an ethyl group.

According to further features in preferred embodiments of the general formula of the compound described below, the unsaturated hydrocarbyl is an ethylene group.

According to further features in preferred embodiments of the general formula of the compound described below, the aromatic system is a pyridine ring.

According to further features in preferred embodiments of the general formula of the compound described below, including the ($R_nY$—T) group as the donor group, the Y is a the heteroatom selected from the group consisting of nitrogen, oxygen, sulfur, and phosphorous.

According to further features in preferred embodiments of the general formula of the compound described below, including the ($R_nY$—T) group as the donor group, the optional $R_n$ substituents are the at least one saturated substituent selected from the group consisting of a methyl substituent and an ethyl substituent.

According to further features in preferred embodiments of the general formula of the compound described below, including the ($R_nY$—T) group as the donor group, the optional $R_n$ substituents are the at least one unsaturated substituent, the unsaturated substituent includes a part of an aromatic system.

According to further features in preferred embodiments of the general formula of the compound described below, the compound is used as part of a catalyst for catalytic polymerization of an alpha-olefin monomer.

According to further features in preferred embodiments of the general formula of the compound described below, the compound is used as a pre-catalyst activated by a co-catalyst for catalytic polymerization of an alpha-olefin monomer.

According to another aspect of the present invention, there is provided a method for catalytic polymerization of an alpha-olefin monomer comprising the steps of: (a) providing a pre-catalyst having a general structure selected from the group consisting of:

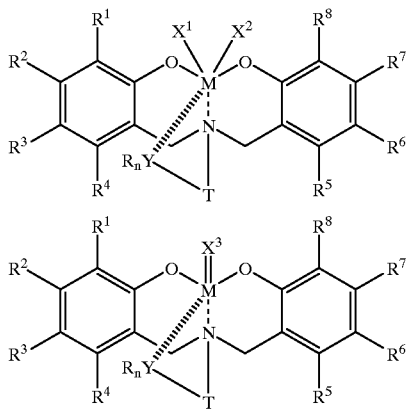

wherein: a solid line represents a covalent bond; a dashed line represents a bond having a varying degree of covalency and a varying degree of coordination; M is a metal atom covalently bonded to each O atom and bonded with varying degrees of covalency and coordination to the N atom; $X^1$ and $X^2$ are each a univalent anionic ligand covalently bonded to the metal atom; $X^3$ is a single divalent anionic ligand covalently bonded to the metal atom; $R^1$ through $R^4$ are each a univalent radical covalently bonded to first ($C_6$) aromatic group; $R^5$ through $R^8$ are each a univalent radical covalently bonded to second ($C_6$) aromatic group; and ($R_n$Y—T) is an optional group selected from the group consisting of a non-donor group covalently bonded to the N atom, wherein the non-donor group, T is a covalent bridging group between the N atom and Y, the Y is a group covalently bonded to the T, and, each of at least one $R_n$ is selected from the group consisting of a saturated substituent covalently bonded to the Y, an unsaturated substituent covalently bonded to the Y, and a univalent radical covalently bonded to the Y, and a donor group covalently bonded to the N atom, wherein the donor group, T is a covalent bridging group between the N atom and Y, the Y is a heteroatom covalently bonded to the T and bonded with varying degrees of covalency and coordination to the metal atom, and, optional Rn substituents are selected from the group consisting of at least one saturated substituent covalently bonded to the Y, and at least one unsaturated substituent covalently bonded to the Y; (b) dissolving the pre-catalyst in a first organic solvent for forming a solution of the pre-catalyst; (c) providing a cocatalyst for activating the pre-catalyst; (d) dissolving the co-catalyst in a second organic solvent for forming a solution of the co-catalyst; (e) combining the solution of the pre-catalyst and the solution of the co-catalyst with the alpha-olefin monomer for forming a polymerization reaction system wherein the co-catalyst activates the pre-catalyst, such that the combination becomes a catalyst for effecting the catalytic polymerization of the alpha-olefin monomer and for producing at least one type of poly(alpha-olefin) product; (f) allowing the polymerization reaction of the alpha-olefin monomer effected by the catalyst to come to a completion; and (g) isolating the at least one type of the poly(alpha-olefin) product.

According to further features in preferred embodiments of the method described below, wherein the pre-catalyst, the metal atom is a transition metal atom.

According to further features in preferred embodiments of the method described below, wherein the pre-catalyst, the transition metal atom is selected from the group consisting of zirconium, hafnium and titanium.

According to another aspect of the present invention, there is provided a method for catalytic polymerization of an alpha-olefin monomer comprising the steps of: (a) providing a pre-catalyst having a general structure selected from the group consisting of:

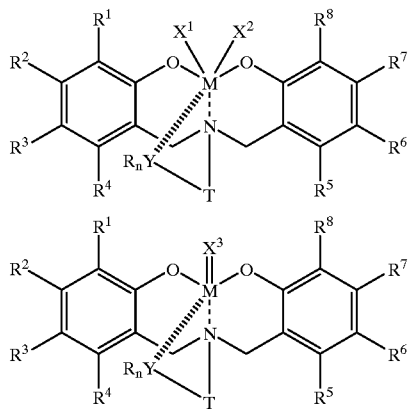

wherein: a solid line represents a covalent bond; a dashed line represents a bond having a varying degree of covalency and a varying degree of coordination; M is a metal atom covalently bonded to each O atom and bonded with varying degrees of covalency and coordination to the N atom; $X^1$ and $X^2$ are each a univalent anionic ligand covalently bonded to the metal atom; $X^3$ is a single divalent anionic ligand covalently bonded to the metal atom; $R^1$ through $R^4$ are each a univalent radical covalently bonded to first ($C_6$) aromatic group; $R^5$ through $R^8$ are each a univalent radical covalently bonded to second ($C_6$) aromatic group; and ($R_n$Y—T) is an optional group selected from the group consisting of a non-donor group covalently bonded to the N atom, wherein the non-donor group, T is a covalent bridging group between the N atom and Y, the Y is a group covalently bonded to the T, and, each of at least one $R_n$ is selected from the group consisting of a saturated substituent covalently bonded to the Y, an unsaturated substituent covalently bonded to the Y, and a univalent radical covalently bonded to the Y, and a donor group covalently bonded to the N atom, wherein the donor group, T is a covalent bridging group between the N atom and Y, the Y is a heteroatom covalently bonded to the T and bonded with varying degrees of covalency and coordination to the metal atom, and, optional $R_n$ substituents are selected from the group consisting of at least one saturated substituent covalently bonded to the Y, and at least one unsaturated substituent covalently bonded to the Y; (b) adsorbing the pre-catalyst onto a surface of a solid support for forming an adsorbed form of the pre-catalyst; (c) providing a co-catalyst for activating the adsorbed form of the pre-catalyst; (d)

combining the solid support including the adsorbed form of the pre-catalyst with the co-catalyst and with the alpha-olefin monomer for forming a polymerization reaction system wherein the co-catalyst activates the adsorbed form of the pre-catalyst such that the combination becomes a catalyst for effecting the catalytic polymerization of the alpha-olefin monomer and for producing at least one type of poly(alpha-olefin) product; (e) allowing the polymerization reaction of the alpha-olefin monomer effected by the catalyst to come to a completion; and (f) isolating the at least one type of the poly(alpha-olefin) product.

According to further features in preferred embodiments of the method described below, wherein the pre-catalyst, the metal atom is a transition metal atom.

According to further features in preferred embodiments of the method described below, wherein the pre-catalyst, the transition metal atom is selected from the group consisting of zirconium, hafnium and titanium.

The amine bis(phenolate) ligand-metal chelate pre-catalyst of the present invention, when activated by a co-catalyst under mild reaction conditions, is exceptionally reactive for polymerization of a variety of alpha-olefin monomers, including long chain alpha-olefin monomers such as 1-hexene or 1-octene, for forming a variety of poly(alpha-olefin) products such as poly(1-hexene) or poly (1-octene), having high molecular weight and low molecular weight distribution. The amine bis(phenolate) ligand-metal chelate pre-catalyst is relatively stable under commercially applicable conditions for polymerization of alpha-olefin monomers. Moreover, the pre-catalyst, and related forms of the pre-catalyst, of the present invention are relatively simple to synthesize, primarily due to simple syntheses of the corresponding amine bis(2-hydroxyarylmethyl) ligand precursors from a variety of commercially available inexpensive starting materials, compared to syntheses of metallocene type pre-catalysts.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
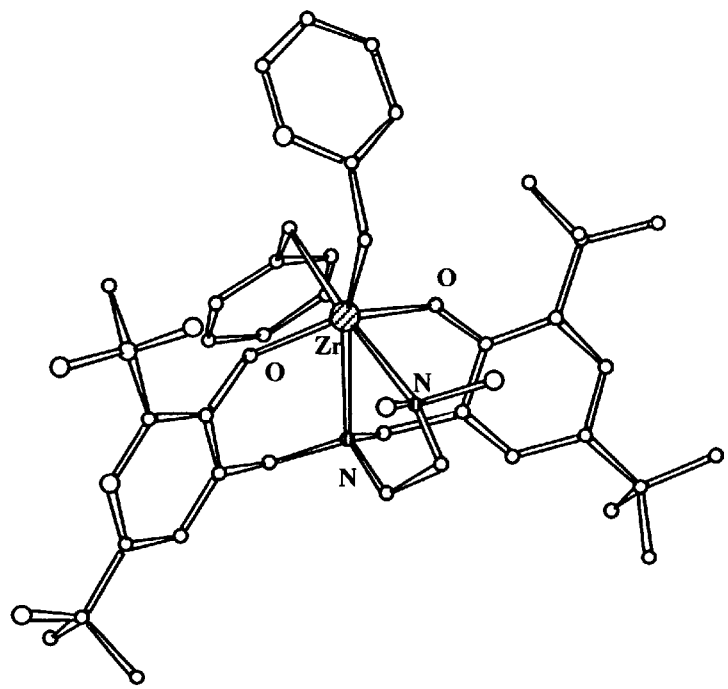
FIG. 1 is an illustration of the X-ray structure of six coordinate dialkyl amine bis(phenolate) ligand-metal chelate pre-catalyst [(CH$_3$)$_2$N—CH$_2$—CH$_2$—]—Zr(CH$_2$Ph)$_2$ 9.

The present invention relates to catalytic polymerization of alpha-olefin monomers using an ultra-high activity non-metallocene pre-catalyst featuring an amine bis(phenolate) ligand-metal chelate and a corresponding method. The amine bis(phenolate) ligand-metal chelate pre-catalyst of the present invention, when activated by a co-catalyst under mild reaction conditions, is at least one order of magnitude more reactive for polymerization of a variety of alpha-olefin monomers compared to polymerization of alpha-olefin monomers using metallocene or metallocene type pre-catalysts. The amine bis(phenolate) ligand-metal chelate pre-catalyst polymerizes long chain alpha-olefin monomers such as 1-hexene or 1-octene, for forming a variety of poly(alpha-olefin) products such as poly(1-hexene) or poly (1-octene), having high molecular weight and low molecular weight distribution. The amine bis(phenolate) ligand-metal chelate pre-catalyst is relatively stable under commercially applicable conditions for polymerization of alpha-olefin monomers. Moreover, this pre-catalyst is relatively simple to synthesize, and is considered more available compared to currently used metallocene type pre-catalysts.

It is to be understood that the invention is not limited in its application with respect to details of exemplary chemical structures, formulas, and procedures set forth in the following description, drawings, or examples. The invention is capable of other embodiments or of being practiced or carried out in various ways. Also, it is to be understood that the phraseology and terminology employed herein is for the purpose of description and should not be regarded as limiting.

General Structures and Formulas of the Amine Bis (phenolate) Ligand-Metal Chelate Pre-catalyst The preferred embodiment of the amine bis(phenolate) ligand-metal chelate pre-catalyst of the present invention is either general structure 1 or general structure 2:

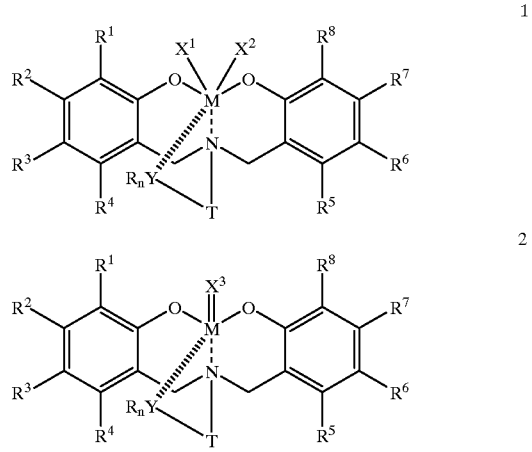

wherein a solid line represents a covalent bond and a dashed line represents a bond varying in degree of covalency and coordination between the indicated atoms; 'M' is a metal atom covalently bonded to each O atom and bonded with varying degrees of covalency and coordination to the N atom, as shown in structures 1 and 2 by the dashed line between the metal atom, M, and the N atom, such as a transition metal atom including zirconium, hafnium or titanium; $X^1$ and $X^2$ are each a univalent anionic ligand covalently bonded to the metal atom, M, such as a halide, a hydride, a saturated or unsaturated hydrocarbyl, an alkoxide, an aryloxide, a dialkylamide, or an arylamide; $R^1$ through $R^4$ are each a univalent radical covalently bonded to the first ($C_6$) aromatic group, such as a hydrogen, hydrocarbyl, or any other univalent radical like an alkoxide; $R^5$ through $R^8$ are each a univalent radical covalently bonded to the second ($C_6$) aromatic group, such as a hydrogen, hydrocarbyl, or any other univalent radical like an alkoxide.

($R_nY$—T) is an optional group in each of the two general structures 1 and 2, and is selected from the group consisting of a non-donor group covalently bonded to the N atom, where, in the non-donor group, 'T' is a covalent bridging group between the N atom and 'Y', such as a saturated hydrocarbyl, or an unsaturated hydrocarbyl, 'Y' is a group covalently bonded to T such as a saturated hydrocarbyl or an unsaturated hydrocarbyl, and, each of at least one $R_n$ is selected from the group consisting of a saturated substituent covalently bonded to Y, such as a methyl substituent or an ethyl substituent, an unsaturated substituent covalently bonded to Y, and a univalent radical covalently bonded to Y, such as a hydrogen radical or a methyl radical, and a donor group covalently bonded to the N atom, where, in the donor group, 'T' is a covalent bridging group between the N atom and 'Y', such as a saturated hydrocarbyl, an unsaturated hydrocarbyl, or a part of an aromatic system such as pyridine, 'Y' is a heteroatom covalently bonded to T and bonded with varying degrees of covalency and coordination to the metal atom, M, as shown in structures 1 and 2 by the dashed line between Y and the metal atom, M, such as nitrogen, oxygen, sulfur or phosphorous, and, optional $R_n$ substituents are selected from the group consisting of at least one saturated substituent covalently bonded to Y, such as a methyl or an ethyl substituent, and at least one unsaturated substituent covalently bonded to Y, such as part of an aromatic system.

In the case that the group ($R_nY$—T) is not present in either general structure 1 or 2 of the pre-catalyst of the present invention, the metal atom, M, is capable of forming a pure covalent bond to the N atom, whereby, the dashed line is replaced by a solid line between metal atom, M, and the N atom.

In an alternative preferred embodiment of the general structure of the amine bis(phenolate) ligand-metal chelate pre-catalyst 1 of the present invention, univalent anionic ligands $X^1$ and $X^2$ are replaced by ligand $X^3$, a single divalent anionic ligand covalently bonded to the metal, M, such as a cyclometallated hydrocarbyl, or a radical such as an alkylidene, resulting in alternative general structure of the amine bis(phenolate) ligand-metal chelate pre-catalyst 2 of the present invention.

General formulas corresponding to general structures 1 and 2 of amine bis(phenolate) ligand-metal chelate pre-catalyst of the present invention are as follows:

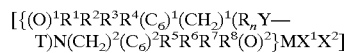

and

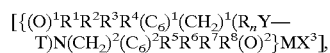

respectively.

As previously described with respect to general structures 1 and 2 of the pre-catalyst of the present invention, here, 'M' is a metal atom covalently bonded to each O atom, $(O)^1$ and $(O)^{2,}$ and bonded to the N atom with varying degrees of covalency and coordination, as shown in general structures 1 and 2 by the dashed line between the metal atom, M, and the N atom, such as a transition metal atom including zirconium, hafnium or titanium; $X^1$ and $X^2$ are each a univalent anionic ligand covalently bonded to the metal atom, M, such as a halide, a hydride, a saturated or unsaturated hydrocarbyl, an alkoxide, an aryloxide, an dialkylamide, or an arylamide; $X^3$ is a single divalent anionic ligand covalently bonded to the metal atom, M, such as a cyclometallated hydrocarbyl, or a radical such as an alkylidene; $R^1$ through $R^4$ are each a univalent radical covalently bonded to the first ($C_6$) aromatic group, $(C_6)^1$, such as a hydrogen, hydrocarbyl, or any other univalent radical like an alkoxide; $R^5$ through $R^8$ are each a univalent radical covalently bonded to the second ($C_6$) aromatic group, $(C_6)^2$, such as a hydrogen, hydrocarbyl, or any other univalent radical like an alkoxide.

($R_nY$—T) is an optional group in each of the two general structures 1 and 2, and is selected from the group consisting of a non-donor group covalently bonded to the N atom, where, in the non-donor group, 'T' is a covalent bridging group between the N atom and 'Y', such as a saturated hydrocarbyl, or an unsaturated hydrocarbyl, 'Y' is a group covalently bonded to T such as a saturated hydrocarbyl or an unsaturated hydrocarbyl, and, each of at least one $R_n$ is selected from the group consisting of a saturated substituent covalently bonded to Y, such as a methyl substituent or an ethyl substituent, an unsaturated substituent covalently bonded to Y, and a univalent radical covalently bonded to Y, such as a hydrogen radical or a methyl radical, and a donor group covalently bonded to the N atom, where, in the donor group, 'T' is a covalent bridging group between the N atom and 'Y', such as a saturated hydrocarbyl, an unsaturated hydrocarbyl, or a part of an aromatic system such as pyridine, 'Y' is a heteroatom covalently bonded to T and bonded with varying degrees of covalency and coordination to the metal atom, M, as shown in structures 1 and 2 by the dashed line between Y and the metal atom, M, such as nitrogen, oxygen, sulfur or phosphorous, and, optional $R_n$ substituents are selected from the group consisting of at least one saturated substituent covalently bonded to Y, such as a methyl or an ethyl substituent, and at least one unsaturated substituent covalently bonded to Y, such as part of an aromatic system.

In the case that the group ($R_nY$—T) is not present in either general formula of the pre-catalyst of the present invention, the metal atom, M, is capable of forming a pure covalent bond to the N atom.

Synthesis of Amine Bis(2-hydroxyarylmethyl), General Ligand Precursor

Synthesis of the general ligand precursor, amine bis(2-hydroxyarylmethyl) 6, described below and used for synthesizing different related forms of the amine bis(phenolate) ligand-metal chelate pre-catalyst of the present invention, is taught by Burke, W. J. et al., in *J. Org. Chem.* 29, 909, 1964. The inventors synthesized different forms of general ligand precursor 6 using a modified Mannich reaction between a primary amine 3, formaldehyde 4, and substituted phenols 5A and 5B.

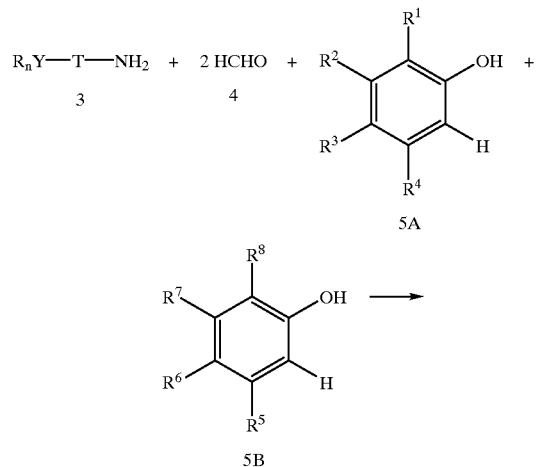

-continued

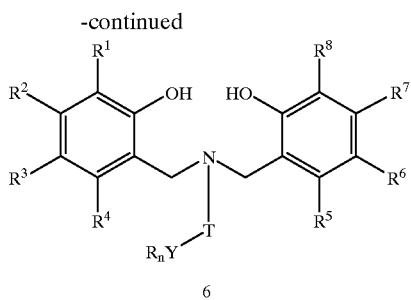

6

The structure of amine bis(2-hydroxyarylmethyl) general ligand precursor 6 features two hydroxyaryl rings, wherein the hydroxyaryl rings include a variety of substituents $R^1$ through $R^8$. Substituents $R^1$ through $R^4$ are each a univalent radical covalently bonded to the first hydroxyaryl ring, such as a hydrogen, hydrocarbyl, or any other univalent radical like an alkoxide, and substituents $R^5$ through $R^8$ are each a univalent radical covalently bonded to the second hydroxyaryl ring, such as a hydrogen, hydrocarbyl, or any other univalent radical like an alkoxide.

The two hydroxyaryl rings are bridged by a bridging group —$CH_2$—($R_nY$—T)N—$CH_2$—. The bridging group, —$CH_2$—($R_nY$—T)N—$CH_2$—, includes the group ($R_nY$—T), wherein as described above, ($R_nY$—T) is either of two general forms, and is selected from the group consisting of a non-donor group covalently bonded to the N atom, where, in the non-donor group, 'T' is a covalent bridging group between the N atom and 'Y', such as a saturated hydrocarbyl, or an unsaturated hydrocarbyl, 'Y' is a group covalently bonded to T such as a saturated hydrocarbyl or an unsaturated hydrocarbyl, and, each of at least one $R_n$ is selected from the group consisting of a saturated substituent covalently bonded to Y, such as a methyl substituent or an ethyl substituent, an unsaturated substituent covalently bonded to Y, and a univalent radical covalently bonded to Y, such as a hydrogen radical or a methyl radical, and a donor group covalently bonded to the N atom, where, in the donor group, T is a covalent bridging group between the N atom and Y, such as a saturated hydrocarbyl, an unsaturated hydrocarbyl, or a part of an aromatic system such as pyridine, Y is a heteroatom covalently bonded to T, such as nitrogen, oxygen, sulfur or phosphorous, and, optional $R_n$ substituents are selected from the group consisting of at least one saturated substituent covalently bonded to Y, such as a methyl substituent or an ethyl substituent, and at least one unsaturated substituent covalently bonded to Y, such as part of an aromatic system, for example, pyridine. Each different form of the group ($R_nY$—T) covalently bonded to the N atom, typically extends from the N atom with a different characteristic length.

Three specific examples of the bridging group, —$CH_2$—($R_nY$—T)N—$CH_2$—, each including a different form of the optional group ($R_nY$—T), are (i) where ($R_nY$—T) is the donor group [$(CH_3)_2N$—$CH_2$—$CH_2$—], wherein T is saturated hydrocarbyl, —$CH_2$—$CH_2$—, covalently bonded to the N atom of the bridging group and covalently bonded to Y, where Y is heteroatom N, and two $R_n$ saturated substituents are two methyl substituents, (—$CH_3$)$_2$, each covalently bonded to donor group N atom; (ii) where ($R_nY$—T) is the non-donor group [$CH_3$—$CH_2$—$CH_2$—], without a heteroatom, wherein T is saturated hydrocarbyl, —$CH_2$—$CH_2$—, covalently bonded to the N atom of the bridging group and covalently bonded to Y, Y is methylene group, —$CH_2$—, and a single $R_n$ substituent is a hydrogen radical covalently bonded to the methylene group; and, (iii) where ($R_nY$—T) is the donor group [$(C_5H_4N)$—$CH_2$—], wherein T is unsaturated hydrocarbyl, —$CH_2$—C—, covalently bonded to the N atom of the bridging group and covalently bonded to Y, and, Y is heteroatom N, which along with a single four-carbon $R_n$ substituent form part of a pyridine aromatic ring system, where pyridine is covalently bonded to the —$CH_2$— part of T, via carbon at pyridine position number 2. Details of the syntheses and spectroscopic data of the resulting structures of different forms of the amine bis(2-hydroxyarylmethyl) general ligand precursor 6, corresponding to each exemplary form of the bridging group including a different form of the group ($R_nY$—T) are provided in Examples 1, 2, and 3, respectively, below.

Synthesis of Amine Bis(phenolate) Ligand-metal Chelate Pre-catalysts

Amine bis(2-hydroxyarylmethyl) general ligand precursor 6 is targeted for binding to a metal, such as a transition metal including zirconium, titanium, and hafnium, for synthesizing different forms of amine bis(phenolate) ligand-metal chelate pre-catalyst 1 or 2, in accordance to the above descriptions. Amine bis(2-hydroxyarylmethyl) general ligand precursor 6 reacts, under variable reaction conditions, with one equivalent of a transition metal complex such as zirconium tetra(benzyl), zirconium tetrakis(dimethylamide), titanium tetra(isopropoxide) or hafnium tetra(chloride), to yield the bis(phenolate)zirconium dibenzyl complex, the bis(phenolate) zirconium bis(dimethylamide) complex, the bis(phenolate)titanium bis(isopropoxide) complex, and the bis(phenolate)hafnium dichloride complex, respectively. Each complex thus formed may be used directly as a pre-catalyst for polymerization of an alpha-olefin monomer, or may be transformed into a pre-catalyst by chemical transformation, such as transformation of amine bis(phenolate)titanium bis(isopropoxide) into amine bis(phenolate)titanium dichloride using a variety of chlorinating reagents, such as trimethylsilylchloride or triethylamine hydrochloride. The amine bis(phenolate)titanium dichloride may be further transformed into an amine bis(phenolate) titanium dialkyl using a variety of alkylating reagents, such as benzyl magnesium chloride or methyl magnesium bromide.

Synthesis of three exemplary forms of the amine bis (phenolate) ligand-metal chelate pre-catalyst 1 of the present invention are generally described here. These exemplary forms of pre-catalyst 1 are distinguished by including a different form of the optional ($R_nY$—T) group, and are referenced with respect to the ($R_nY$—T) group. Further details of each synthesis and, spectroscopic and X-ray data of resulting structures are provided in Examples 4, 5, and 6, respectively, below.

Synthesis of First Exemplary Ligand-metal Chelate Pre-catalyst, [$(CH_3)_2N$—$CH_2$—$CH_2$—]—Zr$(CH_2Ph)_2$ 9

For the first exemplary form of chelate pre-catalyst 1, amine bis(2-hydroxyarylmethyl) specific ligand precursor 7, referenced hereinafter as ligand precursor [$(CH_3)_2N$—$CH_2$—$CH_2$—] 7, is derived from reaction (not shown) of N,N-dimethylethylenediamine, as a specific form of primary amine 3, with formaldehyde 4 and 2,4-di-tert(butyl)phenol, as a specific form of substituted phenols 5A and 5B. Ligand precursor [$(CH_3)_2N$—$CH_2$—$CH_2$—] 7 is a specific form of amine bis(2-hydroxyarylmethyl) general ligand precursor 6, where the bridging group, —$CH_2$—($R_nY$—T)N—$CH_2$—, includes ($R_nY$—T) as donor group, $(CH_3)_2N$—$CH_2$—$CH_2$—, wherein T is saturated hydrocarbyl, —$CH_2$—$CH_2$—, covalently bonded to the N atom of the bridging group and covalently bonded to Y, where Y is heteroatom N, and two $R_n$ saturated substituents are two methyl substituents, (—$CH_3$)$_2$, each covalently bonded to donor group N atom.

Ligand precursor [(CH$_3$)$_2$N—CH$_2$—CH$_2$—] 7 reacts cleanly with one equivalent of zirconium tetra(benzyl), Zr(CH$_2$Ph)$_4$ 8, at 65 C. yielding the six coordinate dialkyl amine bis(phenolate) ligand-metal chelate pre-catalyst 9, also referenced as [(CH$_3$)$_2$N—CH$_2$—CH$_2$—]—Zr(CH$_2$Ph)$_2$ 9, quantitatively as a yellow crystalline solid.

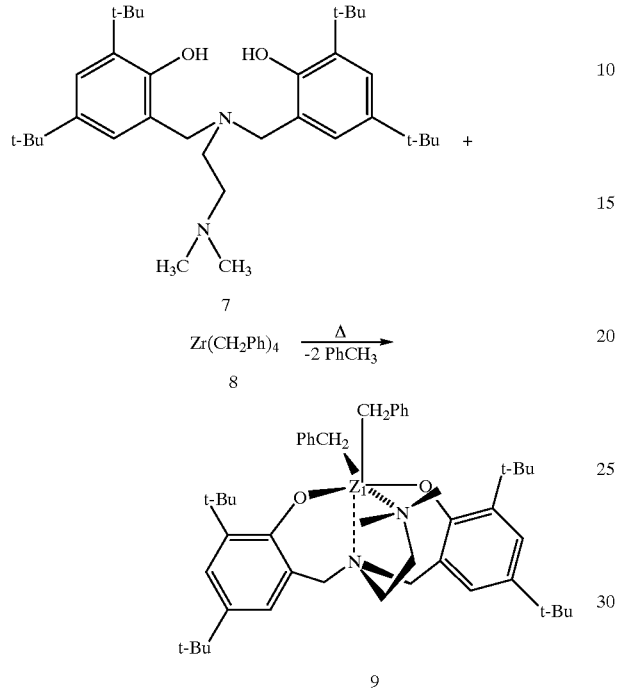

Spectroscopic data of ligand-metal pre-catalyst 9 are consistent with a single stereoisomer featuring symmetrically related phenolate rings, two different benzyl groups, and an AX spin system for the two benzylic methylene groups. This points to a rigid chelate of C$_s$ symmetry on the NMR time scale, with the benzyl groups in a cis geometry, as required for alpha-olefin polymerization catalysts, and the phenolate groups in a trans geometry. The crystallographic (X-ray) structure of pre-catalyst 9 shown in FIG. 1, supports the spectroscopic data, and indicates a structure featuring a mononuclear zirconium chelate having a slightly distorted octahedral geometry, including a coordinative bond between Zr and each of the two nitrogen atoms.

Synthesis of Second Exemplary Ligand-metal Chelate Pre-catalyst, [CH$_3$—CH$_2$—CH$_2$—]—Zr(CH$_2$Ph)$_2$ 11.

For the second exemplary form of chelate pre-catalyst 1, amine bis(2-hydroxyarylmethyl) specific ligand precursor 10, hereinafter referenced as ligand precursor [CH$_3$—CH$_2$—CH$_2$—] 10, is derived from reaction (not shown) of 1-aminopropane, as a specific form of primary amine 3, with formaldehyde 4 and 2,4-di-tert(butyl)phenol, as a specific form of substituted phenols 5A and 5B. Ligand precursor [CH$_3$—CH$_2$—CH$_2$—] 10 is a specific form of amine bis(2-hydroxyarylmethyl) general ligand precursor 6, where the bridging group, —CH$_2$—(R$_n$Y—T)N—CH$_2$—, includes (R$_n$Y—T) as the non-donor group CH$_3$—CH$_2$—CH$_2$—, without a heteroatom, wherein T is saturated hydrocarbyl, —CH$_2$—CH$_2$—, covalently bonded to the N atom of the bridging group and covalently bonded to Y, Y is methylene group, —CH$_2$—, and a single R$_n$ substituent is a hydrogen radical covalently bonded to the methylene group.

Ligand precursor [CH$_3$—CH$_2$—CH$_2$—] 10 reacts cleanly with one equivalent of zirconium tetra(benzyl), Zr(CH$_2$Ph)$_4$ 8, at 65 C. yielding the five coordinate dialkyl amine bis(phenolate) ligand-metal chelate pre-catalyst 11, also referenced as [CH$_3$—CH$_2$—CH$_2$—]—Zr(CH$_2$Ph)$_2$ 11, quantitatively as a colorless crystalline solid.

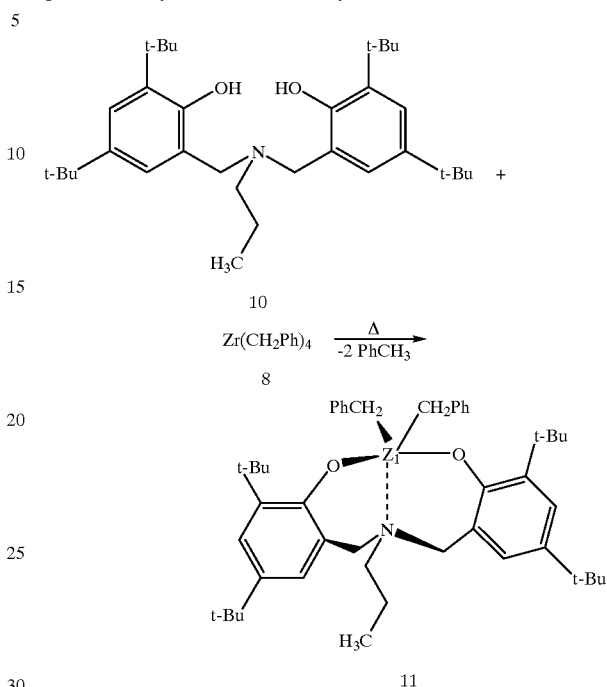

Figure 2:
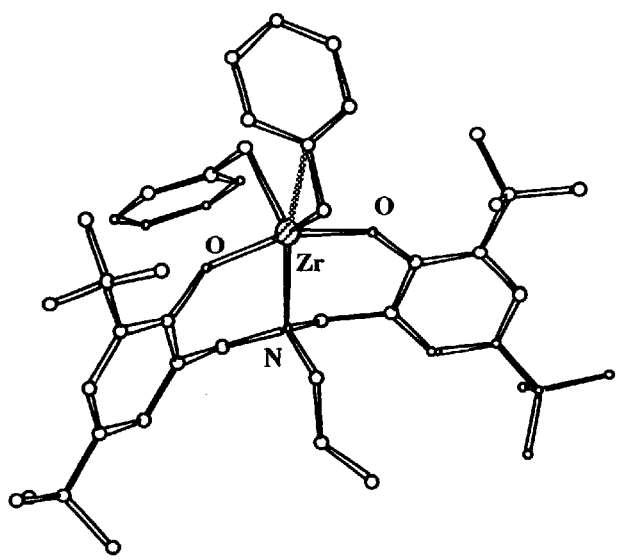
FIG. 2 is an illustration of the X-ray structure of five coordinate dialkyl amine bis(phenolate) ligand-metal chelate pre-catalyst [CH$_3$—CH$_2$—CH$_2$—]—Zr(CH$_2$Ph)$_2$ 11.

Spectroscopic data of ligand-metal pre-catalyst 11 are consistent with a single stereoisomer featuring symmetrically related phenolate rings, two different benzyl groups, and an AX spin system for the two benzylic methylene groups. This points to another rigid chelate of C$_s$ symmetry on the NMR time scale, with the benzyl groups in a non-trans geometry, as required for alpha-olefin polymerization catalysts, and the phenolate groups in a trans geometry. The crystallographic (X-ray) structure of pre-catalyst 11 shown in FIG. 2, supports the spectroscopic data, and indicates a structure featuring a mononuclear zirconium chelate having a pseudo trigonal bi-pyrimidal (TBP) geometry, with axial O atoms and equatorial N, C, C atoms.

In addition to serving as another example of a specific form of amine bis(phenolate) general ligand precursor 6, ligand precursor [CH$_3$—CH$_2$—CH$_2$—] 10 was synthesized for the purpose of synthesizing the five coordinate diallyl amine bis(phenolate) ligand-metal chelate pre-catalyst, [CH$_3$—CH$_2$—CH$_2$—]—Zr(CH$_2$Ph)$_2$ 11, in order to further understand and measure the influence of the 'extra' heteroatom, in donor group (R$_n$Y—T), in the six coordinate dialkyl amine bis(phenolate) ligand-metal chelate pre-catalyst, [(CH$_3$)$_2$ N—CH$_2$—CH$_2$—]—Zr(CH$_2$Ph)$_2$ 9, arising from inclusion of (CH$_3$)$_2$N—CH$_2$—CH$_2$— as donor group (R$_n$Y—T) in the amine bis(phenolate) ligand precursor bridging group, —CH$_2$—(R$_n$Y—T)N—CH$_2$—, for polymerization of alpha-olefin monomers.

Synthesis of Third Exemplary Ligand-metal Chelate Pre-catalyst, [2-Pyridine-CH$_2$—]—Zr(CH$_2$Ph)$_2$ 13

For the third exemplary form of chelate pre-catalyst 1, amine bis(2-hydroxyarylmethyl) specific ligand precursor 12, hereinafter referenced as ligand precursor [2-Pyridine-CH$_2$—] 12, is derived from reaction (not shown) of (2-aminomethyl)pyridine, as a specific form of primary amine 3, with formaldehyde 4 and 2,4-di-tert(butyl)phenol, as a specific form of substituted phenols 5A and 5B. Ligand precursor [2-Pyridine-CH$_2$—] 12 is a specific form of amine bis(2-hydroxyarylmethyl) general ligand precursor 6, where the bridging group, —CH$_2$—(R$_n$Y—T)N—CH$_2$—, includes (R$_n$Y—T) as the donor group (C$_5$H4N)—CH$_2$—, wherein T is unsaturated hydrocarbyl, —CH$_2$—C—, covalently bonded to the N atom of the bridging group and covalently bonded to Y, and, Y is heteroatom N, which along with a single four-carbon R$_n$ substituent form part of a pyridine aromatic ring system, where pyridine is covalently bonded to the —CH$_2$— part of T, via carbon at pyridine position number 2.

Ligand precursor [2-Pyridine-CH$_2$—] 12 reacts cleanly with one equivalent of zirconium tetra(benzyl), Zr(CH$_2$Ph)$_4$ 8, at 65 C. yielding the six coordinate dialkyl amine bis (phenolate) ligand-metal chelate pre-catalyst 13, also referenced as [2-Pyridine-CH$_2$—]—Zr(CH$_2$Ph)$_2$ 13, quantitatively as a yellow crystalline solid.

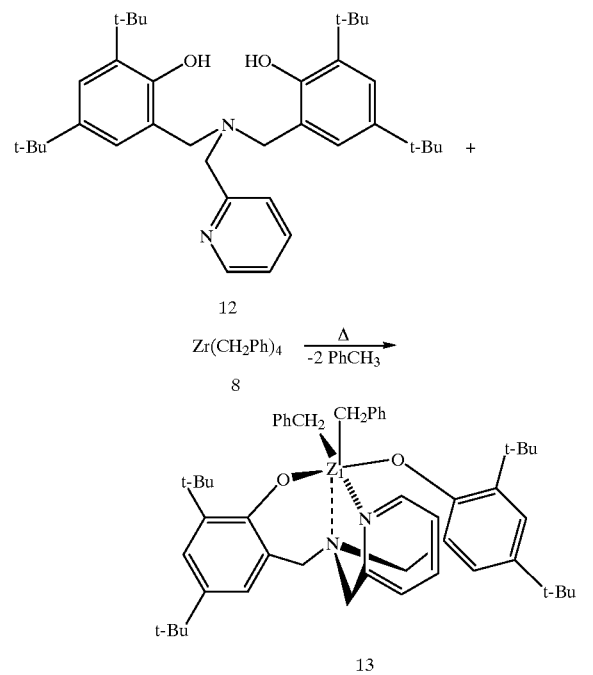

Spectroscopic data of ligand-metal pre-catalyst 13 are consistent with a single stereoisomer featuring symmetrically related phenolate rings, two different benzyl groups, and an AX spin system for the two benzylic methylene groups. This points to a rigid chelate of C$_s$ symmetry on the NMR time scale, with the benzyl groups in a cis geometry, as required for alpha-olefin polymerization catalysts, and the phenolate groups in a trans geometry.

Method for Polymerization of Alpha-olefin Monomers

The method for polymerization of alpha-olefin monomers according to the present invention is herein generally described with respect to using any specific form of the amine bis(phenolate) ligand-metal chelate pre-catalyst 1 or 2, including the three exemplary specific forms of pre-catalyst 1 as described above, namely, dialkyl amine bis (phenolate) ligand-metal chelate pre-catalyst [(CH$_3$)$_2$N—CH$_2$—CH$_2$—]—Zr(CH$_2$Ph)$_2$ 9, dialkyl amine bis (phenolate) ligand-metal chelate pre-catalyst [CH$_3$—CH$_2$—CH$_2$—]—Zr(CH$_2$Ph)$_2$ 11, or, dialkyl amine bis(phenolate) ligand-metal chelate pre-catalyst [2-Pyridine-CH$_2$—]—Zr (CH$_2$Ph)$_2$ 13, respectively. Details of polymerization of an exemplary specific alpha-olefin, 1-hexene, using each of the three exemplary forms of the amine bis(phenolate) ligand-metal chelate pre-catalyst 9, 11, or 13, for forming poly(1-hexene) product, and related empirical data thereof, are provided in Examples 7 and 8, 9, and 10, respectively, below.

In Step 1 of the method for polymerization of an alpha-olefin monomer, a quantity of a specific form of amine bis(phenolate) ligand-metal chelate pre-catalyst 1 or 2 is dissolved in an organic solvent. Any non-protic organic solvent may be used which is capable of dissolving, without decomposing, pre-catalyst 1 or 2. Preferably, the organic solvent is selected from the group including the alpha-olefin monomer to be polymerized such as 1-pentene, 1-hexene, or 1-octene, or, an organic solvent such as pentane, heptane, toluene, methylene chloride, and chlorobenzene.

In Step 2, a co-catalyst, required for activation of pre-catalyst 1 or 2, is dissolved in an organic solvent. The co-catalyst is selected from the group including but not limited to, for example, a boron Lewis acid such as tris (penta-fluoro-phenyl)boron, B(C$_6$F$_5$)$_3$, a boron salt such as N,N'-dimethyl anilinium tetra(penta-fluoro-phenyl)borate, [Ph(CH$_3$)$_2$NH][B(C$_6$F$_5$)$_4$], and an aluminum compound such as methylaluminoxane (MAO). Any organic solvent may be used which is capable of dissolving, without decomposing, the selected co-catalyst. Preferably, the organic solvent is selected from the group including the alpha-olefin monomer to be polymerized such as 1-pentene, 1-hexene or 1-octene, or, an organic solvent such as pentane, heptane, toluene, methylene chloride, and chlorobenzene.

The specific solvent or solvents used for dissolving amine bis(phenolate) ligand-metal chelate pre-catalyst 1 or 2, and for dissolving the co-catalyst, depend upon the desired poly(alpha-olefin) product distribution, especially with respect to formation of different homo-polymers and co-polymers, each having a different degree of alpha-olefin monomer incorporation. Typically, when the monomer to be polymerized is liquid phase, at least one of the solvents used for dissolving amine bis(phenolate) ligand-metal chelate pre-catalyst 1 or 2 and/or the co-catalyst is the alpha-olefin monomer targeted as the desired poly(alpha-olefin) product. Molecular weight distribution, measured as PDI, of the product formed is typically affected by the concentration of the alpha-olefin monomer to be polymerized in a solvent including inert diluent, such as pentane or heptane. For example, when the alpha-olefin polymerization is conducted in neat 1-hexene, a temperature rise may occur, due to exothermic reaction, generally resulting in a relatively broad polymer molecular weight distribution, leading to a relatively high PDI value. When the same alpha-olefin polymerization is conducted under similar conditions, but using dilute solution of the target 1-hexene and inert diluent such as heptane, reaction temperature rise is milder, and polymer molecular weight distribution is narrower, yielding a lower PDI value.

In Step 3A, the dissolved co-catalyst is added to or combined with the dissolved amine bis(phenolate) ligand-metal chelate pre-catalyst 1 or 2, for forming a polymerization reaction system.

Conditions for performing Step 1 through Step 3 are preferably room temperature, with exclusion of moisture and oxygen in order to prevent hydrolysis or oxidation of either the pre-catalyst or the co-catalyst.

As an alternative step for including the alpha-olefin monomer as one of the solvents used for dissolving amine bis(phenolate) ligand-metal chelate pre-catalyst 1 or 2, or for dissolving the co-catalyst, is Step 3B, where the desired alpha-olefin monomer is separately added as a gas phase reactant, bubbled into and/or through the liquid phase already including dissolved amine bis(phenolate) ligand-metal chelate pre-catalyst 1 or 2 and co-catalyst, for forming the polymerization reaction system.

In Step 4, the polymerization reaction system is stirred for a duration in the range of between about 30 seconds to about 12 hours. Starting from olymerization reaction initiation, and including duration of stirring of the reaction system, heat may be released from the reaction system, accompanied by possible color change of the reaction system. The polymerization may be conducted at different temperatures. External cooling, for example, down to about 0 C., may be used for slowing down the polymerization. Heating, for example, to reflux temperature, speeds up the reaction.

In Step 5, the polymerization reaction is finished under one of the following cases: (i) stopping the polymerization reaction by addition of an external quencher such as a protic solvent; (ii) complete consumption of the monomer; (iii) termination of the polymerization reaction due to catalyst deactivation.

In Step 6, the polymer product is isolated by the following procedure. Excess pre-catalyst 1 or 2 and/or co-catalyst, may be hydrolyzed. Isolation of the polymer product from the solvent and/or remaining alpha-olefin monomer in solution depends upon the solubility of the polymer product. In the case of an insoluble polymer product, for example, polyethylene, the isolation procedure includes filtration and drying, whereas in the case of a soluble polymer product, volatile species are removed by distillation and the polymer product is then dried. Impurities, such as decomposition products of pre-catalyst 1 or 2 and/or co-catalyst are typically washed away.

In Step 7, physicochemical properties and characteristics of the poly(alpha-olefin) products produced from the polymerization reaction system are measured and analyzed by various techniques, including melting point, pectroscopy such as NMR, mechanical strength such as elasticity, etc. Structural information and molecular weight information relating to polymer molecular weight distribution via the polydispersity index (PDI), are also determined.

In an alternative preferred embodiment of the method for catalytic polymerization of an alpha-olefin monomer, using amine bis(phenolate) ligand-metal chelate pre-catalyst 1 or 2 of the present invention, a specific form of chelate pre-catalyst 1 or 2 is adsorbed onto the surface of a solid support such as silica, alumina, or magnesia. A suitable co-catalyst, such as one of the co-catalysts previously described in Step 2, is combined with the adsorbed pre-catalyst on the surface of the solid support. The co-catalyst is brought into contact with adsorbed pre-catalyst by a variety of ways, including by adsorbing co-catalyst on the same surface of the solid support used for adsorbing pre-catalyst, by flowing a solution of dissolved co-catalyst through a catalytic reactor bed housing the solid support featuring the adsorbed pre-catalyst, or by pouring a specified volume of solution of dissolved co-catalyst onto the solid support featuring the adsorbed pre-catalyst.

Once in contact, interaction of adsorbed pre-catalyst 1 or 2 and co-catalyst enables activation of pre-catalyst, and the combination of pre-catalyst and co-catalyst results in formation of a combined or complex catalyst for heterogeneous catalytic polymerization of an alpha-olefin monomer. Here, an alpha-olefin monomer reactant is fed to the catalyst as either liquid or gas phase, and the ensuing heterogeneous gas or liquid/solid phase polymerization reaction takes place on the surface of the heterogeneous catalyst at the location of adsorbed activated pre-catalyst 1 or 2.

To illustrate the ultra-high catalytic activity exhibited by amine bis(phenolate) ligand-metal chelate pre-catalyst 1 of the present invention for polymerization of alpha-olefin monomers, highlights of selected polymerization reaction systems described in Examples 7–10 below are herein provided.

Amine bis(phenolate) ligand-metal chelate pre-catalyst 1 in the first exemplary specific form described above, namely, six coordinate dialkyl amine bis(phenolate) ligand-metal chelate pre-catalyst $[(CH_3)_2N—CH_2—CH_2—]—Zr(CH_2Ph)_2$ 9, is activated by boron Lewis acid co-catalyst, $B(C_6F_5)_3$, in the presence of neat 1-hexene at room temperature under nitrogen gas inert atmosphere, where 1-hexene functions as both the target alpha-olefin monomer to be polymerized and as dissolution solvent for pre-catalyst 9 and for the boron co-catalyst.

Unexpectedly, the ensuing reaction resulted in dramatic generation of exothermic heat, resulting in boiling of the 1-hexene monomer at 64° C., and extremely rapid formation of poly(1-hexene) product. Consumption of the 1-hexene monomer was essentially complete after only about 2 minutes. Average molecular weight of the poly(1-bexene) product was measured as $M_w$=12,700 grams/mole, and the PDI was 6. The relatively broad molecular weight distribution may be caused by the relatively high temperature of the olymerization mixture arising from a relatively high rate of exothermic heat valved under these reaction conditions.

For this catalytic polymerization system, catalytic activity of pre-catalyst 9 was calculated from reaction data as 15,500 (grams poly(1-hexene) produced)/(mmole-pre-cat. hr). This magnitude of catalytic activity of a non-metallocene type pre-catalyst for catalytic polymerization of an alpha-olefin monomer is exceptionally high considering the relatively unfavorable polymerization reaction conditions involving use of a small quantity of a moderately active, non-MAO, boron co-catalyst, and where labile groups in polymerization pre-catalyst 9 are benzyl groups.

When the same pre-catalyst $[(CH_3)_2N—CH_2—CH_2—]—Zr(CH_2Ph)_2$ 9 is activated by the same boron Lewis acid co-catalyst, $B(C_6F_5)_3$, in 1-hexene diluted with heptane diluent, to an extent of heptane:1-hexene volume ratio of 7:3, at room temperature under nitrogen gas inert atmosphere, a significantly less vigorous polymerization reaction takes place. Catalytic activity calculated from the reaction data in this case is still relatively high at 2000 (grams poly(1-hexene) produced)/(mmole-pre-cat. hr). Compared to catalytic polymerization of 1-hexene monomer using pre-catalyst 9 activated in neat 1-hexene, exothermic heat evolved by the reaction mixture in dilute 1-hexene was significantly milder, resulting in a substantially lower catalytic activity.

Figure 3:
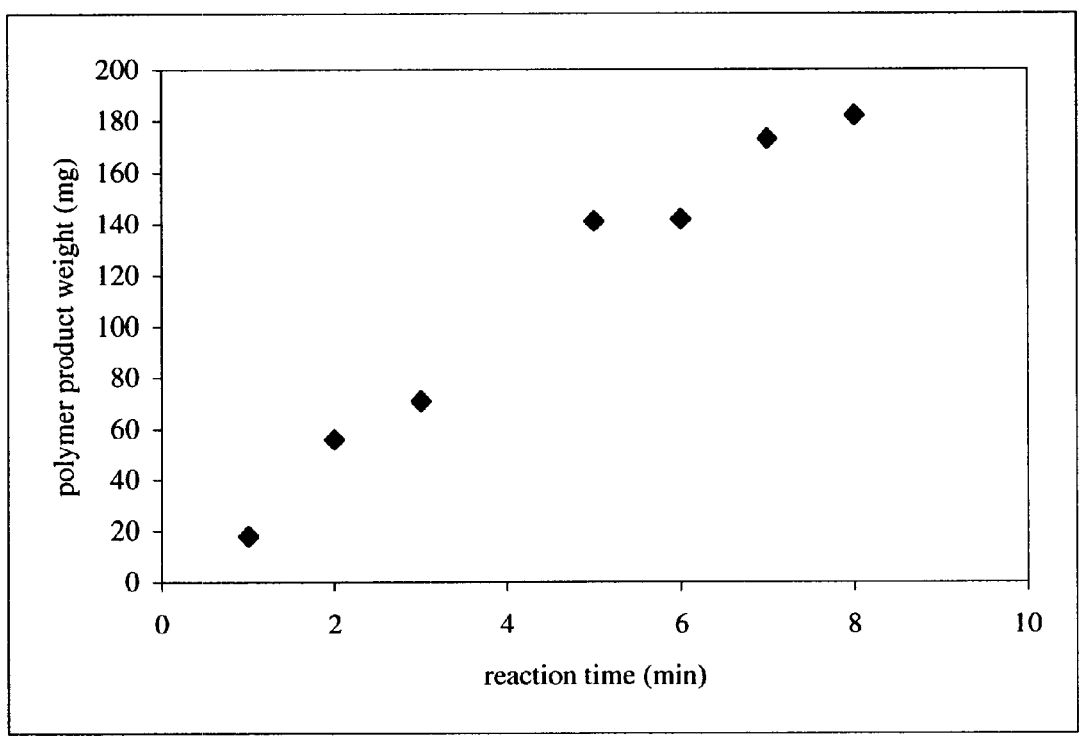
FIG. 3 is an illustration of catalytic activity of amine bis(phenolate) ligand-metal chelate pre-catalyst [(CH$_3$)$_2$N—CH$_2$—CH$_2$—]—Zr(CH$_2$Ph)$_2$ 9 for the polymerization of 1-hexene alpha-olefin monomer in dilute 1-hexene.

In this reaction system, consumption of 1-hexene monomer versus time was measured and found to be linear, as shown in FIG. 3, an illustration of catalytic activity of amine bis(phenolate) ligand-metal chelate pre-catalyst $[(CH_3)_2N—CH_2—CH_2—]—Zr(CH_2Ph)_2$ 9 for the polymerization of 1-hexene alpha-olefin monomer in dilute 1-hexene. The data of FIG. 3 show that this reaction system is active for at least 8 minutes, after which about 80% of the 1-hexene monomer is consumed, under these conditions. The poly(1-hexene) product had a high molecular weight of $M_w$=170,000 grams/mole, with a low PDI of 2.2.

In another example of highly active catalytic polymerization of exemplary alpha-olefin monomer 1-hexene, six coordinate dialkyl amine bis(phenolate) ligand-metal chelate pre-catalyst [2-Pyridine-$CH_2$—]—$Zr(CH_2Ph)_2$ 13 is activated by boron Lewis acid co-catalyst, $B(C_6F_5)_3$, in the presence of neat 1-hexene at room temperature under nitrogen gas inert atmosphere, where again 1-hexene functions as both the target alpha-olefin monomer to be polymerized and as dissolution solvent for pre-catalyst 13 and for the boron co-catalyst. Considerable exothermic heat of reaction is evolved, leading to a catalytic activity calculated from the reaction data of about 10,000 (grams poly(1-hexene) produced)/(mmole-pre-cat. hr). Results of high catalytic activity obtained from this catalytic reaction system, using pre-catalyst 13, are very similar to those obtained when using pre-catalyst 9, for polymerization of 1-hexene alpha-olefin monomer.

Catalytic activity of amine bis(phenolate) ligand-metal chelate pre-catalyst 1 of the present invention, illustrated in part, by specific forms of six coordinate amine bis (phenolate) ligand-metal chelate, pre-catalyst [(CH$_3$)$_2$N—CH$_2$—CH$_2$—]—Zr(CH$_2$Ph)$_2$ 9, and pre-catalyst [2-Pyridine-CH$_2$—]—Zr(CH$_2$Ph)$_2$ 13, operating under the above described reaction conditions, is up to several orders of magnitude higher than catalytic activity of currently used non-metallocene pre-catalysts and related catalytic systems. For example, prior art non-metallocene pre-catalysts and catalytic systems activated by a non-MAO co-catalyst for catalytic polymerization of 1-hexene exhibit catalytic activities of about 400, 200, 40, and 10, grams/(mmole-pre-cat. hr), as reported by Kim, K., in *Organometallics* 17, 3161, 1998, disclosed in U.S. Pat. No. 5,889,128, reported by McConville, D. H., in *J. Am. Chem. Soc.* 118, 10008, 1996, and reported by Schaverien, C. J., in *J. Am. Chem Soc.* 117, 3008, 1995, respectively.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

Reference is now made to the following examples, which together with the above descriptions, illustrate the invention in a non-limiting fashion. Details of the syntheses and spectroscopic data of the resulting structures of three different specific forms of the amine bis(2-hydroxyarylmethyl) general ligand precursor 6, corresponding to each exemplary form of the bridging group, —CH$_2$—(R$_n$Y—T)N—CH$_2$—, including a different form of the group (R$_n$Y—T), are provided in Examples 1, 2, and 3, respectively, below. Details of the syntheses and, spectroscopic and X-ray data of resulting structures of corresponding exemplary forms of the amine bis(phenolate) ligand-metal chelate pre-catalyst 1 of the present invention are provided in Examples 4, 5, and 6, respectively, below.

Details of catalytic polymerization of an exemplary specific alpha-olefin, 1-hexene, using each of the three corresponding exemplary specific forms of amine bis(phenolate) ligand-metal chelate pre-catalyst 1, namely, amine bis (phenolate) ligand-metal chelate pre-catalyst 9, 11, or 13, in accordance with the method of the present invention, for forming poly(1-hexene) product, and related empirical data thereof, are herein provided in Examples 7 and 8, 9, and 10, respectively.

Reference numbers of chemical species and structures appearing in the following examples are identical to those assigned in the above descriptions of the preferred embodiments.

EXAMPLE 1

Synthesis of Amine Bis(2-hydroxyarylmethyl) Ligand Precursor [(CH$_3$)$_2$N—CH$_2$—CH$_2$—] 7

Amine bis(2-hydroxyarylmethyl) ligand precursor [(CH$_3$)$_2$N—CH$_2$—CH$_2$—] 7 was recently prepared in a multi-step procedure and in relatively low yields by Hirotsu, M. et al., in *Bull. Chem. Soc. Jpn.* 70, 649, 1997, using a modification of a method reported by Hinshaw, C. J. et al., in *Inorg. Chem.* 28, 4483, 1989. The following is a moderate yield, one step procedure, which utilizes commercially vailable starting materials.

A solution of 2,4-di-tert(butyl)phenol (5 g, 24.2 mmol), N,N-dimethylethylenediamine (1.8 mL, 16.4 mmol), and 36% aqueous formaldehyde (2.5 mL, 33.6 mmol) in methanol (10 mL), was stirred at room temperature for three days. The mixture was cooled in a freezer over night, filtered, and washed thoroughly with ice cold methanol, to give the bis-adduct 7 as a colorless powder (3.7 g, 58.3% yield), which could be further purified by re-crystallization from methanol.

Melting point of 7 was 158° C.

Spectroscopic Data of 7. $^1$H NMR (C$_6$D$_6$, 200 MHz) δ9.86 (s, 2H, OH), 7.50 (d, J=2.3, 2H, Ar), 6.98 (d, J=2.3, 2H, Ar), 3.39 (s, 4H, CH$_2$), 2.19 (m, 2H, CH$_2$), 1.93 (s, 6H N(CH$_3$)$_2$), 1.67 (s, 18H, C(CH$_3$)$_3$), 1.34 (s, 18H, C(CH$_3$)$_3$), $^{13}$C NMR (CDCl$_3$ 151.14 MHz) δ153.3, 140.1, 136.0, 124.8, 123.3, 121.6, 56.6 (ArCH$_2$N), 56.9 (NCH$_2$), 49.0 (NCH$_2$), 44.8 (N(CH$_3$)$_2$), 35 (C—C), 34.0 (C—C), 31.7 (CH$_3$), 29.5 (CH$_3$).

EXAMPLE 2

Synthesis of Amine Bis(2-hydroxyarylmethyl) Ligand Precursor [CH$_3$—CH$_2$—CH$_2$—] 10

A mixture of 2,4-di-tert(butyl)phenol (5.0 g, 24.2 mmol), 1-aminopropane (1.0 mL, 12.1 mmol), and 36% aqueous formaldehyde (4.0 mL, 48.0 mmol) in methanol (10 mL), was stirred and refluxed for 24 hrs. The mixture was cooled in a freezer over night and the supernatant solution decanted. The residue was triturated using a triturating solvent such as ice cold methanol, filtered, and washed thoroughly with cold methanol, to give the bis-adduct 10 as a colorless powder (2.7 g, 45.4% yield), which could be further purified by re-crystallization from ethanol.

Melting point of 10 was 132° C.

HRMS (high resolution mass spectrometry) of 10: calculated, 495.407630, and observed, 495.406458.

Spectroscopic Data of 10. $^1$H NMR (C$_6$D$_6$, 200 MHz) δ8.21 (s, 2H, OH), 7.48 (d, J=2.3, 2H, Ar), 6.97 (d, J=2.3, 2H, Ar), 3.37 (s, 4H, CH$_2$), 2.19 (t, J=7.1, 2H, CH$_2$), 1.62 (s, 18H, C(CH$_3$)$_3$), 1.34 (s, 18H, C(CH$_3$)$_3$), 1.26 (m, 2H, CH$_2$), 0.57 (t, J=7.3, 3H, CH$_3$). $^{13}$C NMR (CDCl$_3$, 151.14 MHz,) δ152.4, 141.5, 136.0, 125.0, 123, 121, 57.2 (ArCH$_2$N), 55.5 (NCH$_2$), 34.8 (C—C), 34 (C—C), 31.6 (CH$_3$), 29 (CH$_3$), 19.4 (CH$_2$), 11.7 (CH$_3$).

EXAMPLE 3

Synthesis of Amine Bis(2-hydroxyarylmethyl) Ligand Precursor [2-Pyridine-CH$_2$—] 12

A solution of 2,4-di-tert(butyl)phenol (5.0 g, 24.2 mmol), 2-(aminomethyl)pyridine (1.5 mL, 14.6 mmol) and 36% aqueous formaldehyde (2 mL, 24 mmol) in methanol (8 mL) was stirred and refluxed for 18 hrs. The mixture was cooled in a freezer over night and the supernatant solution decanted. The solid residue was triturated with ice cold methanol, filtered, and washed thoroughly with cold methanol, to give the bis-adduct 12 as a colorless powder (2.81 g, 42.6% yield), which could be further purified by recrystallization from methanol.

Melting point of 12 was 199° C.

HRMS of 12: Calculated, 545.410704, and observed, 545.410850.

Spectroscopic Data of 12. $^1$H NMR (acetone-$d_6$, 300 MHz) δ8.71 (d, 1H), 7.85 (t, 1H), 7.43 (t, 1H), 7.35 (d, 1H), 7.03 (d, J=1.2, 2H), 7.23 (d, J=1.2, 2H), 3.92 (s, 2H, NCH$_2$Pr), 3.83 (s, 4H, ArCH$_2$N), 1.39 (s, 18H, C(CH$_3$)$_3$), 1.27 (s, 18H, C(CH$_3$)$_3$). $^{13}$C NMR (CDCl$_3$, 90.68 MHz) δ156.2, 148.1, 137.3, 123.7, 122.4 (5C, pyridine ring), 153.8, 140.4, 136.3, 125.1, 123.4, 121.23 (12C, aromatic), 56.8 (ArCH$_2$N), 55.3 (CH$_2$), 35.06 (C—C), 34.1 (C—C), 31.7 (CH$_3$), 29.6 (CH$_3$).

EXAMPLE 4

Synthesis of Amine Bis(phenolate) Ligand-metal Chelate Pre-catalyst [(CH$_3$)$_2$N—CH$_2$—CH$_2$—]—Zr(CH$_2$Ph)$_2$ 9

A solution of amine bis(2-hydroxyarylmethyl) ligand precursor [(CH$_3$)$_2$N—CH$_2$—CH$_2$—] 7, as synthesized according to Example 1, (200 mg, 0.38 mmol) in toluene (10 mL) was added drop-wise to a solution of zirconium tetra(benzyl) (0.38 mmol) in toluene (10 mL), at room temperature under nitrogen gas inert atmosphere. The reaction mixture was then heated to 65° C. and stirred for two hours. The toluene was removed from the reaction mixture under low pressure to yield pre-catalyst 9, 99% pure, as a yellow solid.

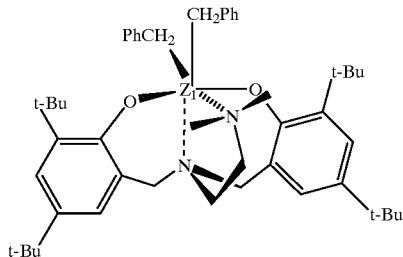

9

Spectroscopic Data of 9. $^1$H NMR (C$_6$D$_6$, 600 MHz) δ7.74 (d, J=7.1, 2H), 7.62 (d, J=2.4, 2H), 7.39 (t, J=8.1, 2H), 7.05 (t, J=7.3, 1H), 6.95 (d, J=2.4, 2H), 6.90 (d, J=7.1, 2H), 6.73 (t, J=8.0, 2H), 6.55 (t, J=7.3, 1H), 3.45 (br d, J=13.0, 2H, CH$_2$), 2.70 (s, 2H, PhCH$_2$), 2.60 (d, J=13.6, 2H, CH$_2$), 2.57 (s, 2H, PhCH$_2$), 1.88 (s, 18H, CH$_3$), 1.48 (s, 6H, N(CH$_3$)$_2$), 1.40 (br, 4H, CH$_2$), 1.36 (s, 18H, CH$_3$). $^{13}$C NMR (C$_6$D$_6$, 151.14 MHz) δ158.2, 149.3, 147.2, 141.3, 136.5, 129.1, 128.4, 128.3, 127.5, 125.2, 124.8, 122.5, 120.4, 68.1 (PhCH$_2$), 66.1 (PhCH$_2$), 65.2 (ArCH$_2$N), 60.2 (NCH$_2$), 51.9 (NCH$_2$), 47.5 (N(CH$_3$)$_2$), 35.7 (C—C), 34.4 (C—C), 32.0 (CH$_3$), 30.8 (CH$_3$).

Crystallographic (X-ray) Data for C$_{53}$H$_{80}$N$_2$O$_2$Zr 9. M=868.41, monoclinic space group P2$_1$/c, a=18.4520(10), b=19.1310(19), c=28.2390(10) Å, β=90°, U=9968.5(8) Å$^3$, Z=8, D$_c$=1.157 g/cm$^3$, μ(Mo—Kα)=0.260 mm$^{-1}$, T=117° K. Enraf-Nonius Kappa-CCD, 9375 reflections were measured (R$_{int}$=0.000). The structure was solved by direct methods and refined by full-matrix least-squares on F$^2$. In the crystal, the dimethylamino(ethyl) arm was found to be disordered. The unit cell contain one molecule of pentane. The final refinement converged at R$_1$=0.1028 and wR$_2$=0.2636 for observations with [I>2σ(I)] and R$_1$=0.1480 and wR$_2$=0.2853 for all data.

Spectroscopic data of 9 are consistent with a single stereoisomer featuring symmetrically related phenolate rings, two different benzyl groups, and an AX spin system for the two benzylic methylene groups. This points to a rigid chelate of C$_s$ symmetry on the NMR time scale, with the benzyl groups in a cis geometry, as required for alpha-olefin polymerization catalysts, and the phenolate groups in a trans geometry.

The crystallographic (X-ray) data support the spectroscopic data. The X-ray structure of pre-catalyst [N(CH$_3$)$_2$—CH$_2$—CH$_2$—]—Zr(CH$_2$Ph)$_2$ 9, shown in FIG. 1, indicates a structure featuring a mononuclear zirconium chelate having a slightly distorted octahedral geometry, including a coordinative bond between Zr and each of the two nitrogen atoms. The phenolate groups of the tetradentate ligand fold back toward the pendant (dimethylamino)ethyl arm to an extent the angle between the two planes of the phenolate rings is about 30 degrees, thus leaving a relatively open cleft for the equatorial benzyl group. The small difference between the two coordinative N—Zr bond lengths may indicate a weaker binding of the outer side arm nitrogen to the metal.

EXAMPLE 5

Synthesis of Amine Bis(phenolate) Ligand-metal Chelate Pre-catalyst [CH$_3$—CH$_2$—CH$_2$—]—Zr(CH$_2$Ph)$_2$ 11

In addition to serving as another example of a specific form of general amine bis(phenolate) ligand-metal chelate pre-catalyst 1, the five coordinate dialkyl amine bis (phenolate) ligand-metal chelate pre-catalyst, [CH$_3$—CH$_2$—CH$_2$—]—Zr(CH$_2$Ph)$_2$ 11, was synthesized in order to further understand and measure the influence of the 'extra' heteroatom, in (R$_n$Y—T) group, in the six coordinate dialkyl amine bis(phenolate) ligand-metal chelate pre-catalyst, [(CH$_3$)$_2$N—CH$_2$—CH$_2$—]—Zr(CH$_2$Ph)$_2$ 9, arising from inclusion of (CH$_3$)$_2$N—CH$_2$—CH$_2$— as (R$_n$Y—T) group in the amine bis(phenolate) ligand precursor bridging group, —CH$_2$—(R$_n$Y—T)N—CH$_2$—, for polymerization of alpha-olefin monomers.

A solution of amine bis(2-hydroxyarylmethyl) ligand precursor [CH$_3$—CH$_2$—CH$_2$—]10, synthesized according to Example 2, (200 mg, 0.40 mmol) in toluene (10 mL) was added drop-wise to a solution of zirconium tetra(benzyl) (0.40 mmol) in toluene (10 mL), at room temperature under nitrogen gas inert atmosphere. The reaction mixture was then heated to 65° C. and stirred for two hours. The color of the reaction mixture changed from yellow to colorless. The toluene was removed from the reaction mixture under low pressure to yield pre-catalyst 11, 99% pure, as a colorless solid.

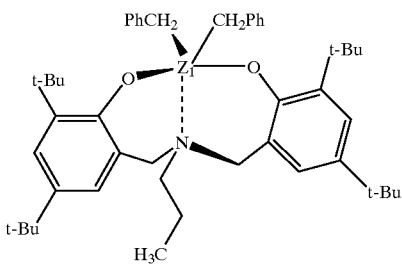

11

Spectroscopic Data of 11. $^1$H NMR (C$_6$D$_6$, 360 MHz) δ7.76 (d, J=7.5, 2H), 7.57 (d, J=2.3, 2H), 7.28 (t, J=7.6, 2H), 7.12 (t, J=7.3, 1H), 6.94 (d, J=2.3, 2H), 6.92 (d, J=7.4, 2H), 6.74 (t, J=7.4, 2H), 6.62 (t, J=7.3, 1H), 3.30 (d, J=13.8, 2H, CH$_2$), 2.99 (s, 2H, PhCH$_2$), 2.98 (d, J=13.6, 2H, CH$_2$), 2.03 (m, 2H, CH$_2$), 1.95 (s, 2H, PhCH$_2$), 1.79 (s, 18H, CH$_3$), 1.35 (s, 18H, CH$_3$), 1.05 (m, 2H, CH$_2$), −0.03 (t, J=7.3, CH$_3$). $^{13}$C NMR (C$_6$D$_6$, 90.68 MHz) δ158.3, 148.3, 142.1, 137.4, 136.8, 131.4, 129.5, 125.8, 125.4, 125.2, 125.1, 122.7, 60.9 (ArCH$_2$N, NCH$_2$), 58.9 (PhCH$_2$), 45.5 (PhCH$_2$), 36.1 (C—C), 35.0 (C—C), 32.6 (CH$_3$), 31.3 (CH$_3$), 14.0 (CH$_2$), 11.2 (CH$_3$).

Crystallographic (X-ray) Data for C$_{54}$H$_{81}$NO$_2$Zr 11. M=867.42, monoclinic space group P2$_1$/c, a=10.4840(1), b=19.2970(4), c=24.5940(5) Å, β=91.048(1)°, U=4974.77 (15) Å$^3$, Z=4, D$_c$=1.158 g/cm$^3$, p(Mo—Kα)=0.259 mm$^{-1}$, T=116° K. Enraf-Nonius Kappa-CCD, 12508 reflections were measured (R$_{int}$=0.000). The structure was solved by direct methods and refined by full-matrix least-squares on F$^2$. In the crystal, one of the tert-butyl groups was found to be disordered. The unit cell contains one molecule of heptane. The final refinement converged at R$_1$=0.0493 and wR$_2$=0.1295 for observations with [I>2σ(I)] and R$_1$=0.0624 and wR$_2$=0.1377 for all data.

Spectroscopic data of 11 are consistent with a single stereoisomer featuring symmetrically related phenolate rings, two different benzyl groups, and an AX spin system for the two benzylic methylene groups. This points to another rigid chelate of C$_s$ symmetry on the NMR time scale, with the benzyl groups in a non-trans geometry, as required for alpha-olefin polymerization catalysts, and the phenolate groups in a trans geometry.

The crystallographic (X-ray) data support the spectroscopic data. The X-ray structure of pre-catalyst [CH$_3$—CH$_2$—CH$_2$—]—Zr(CH$_2$Ph)$_2$ 11, shown in FIG. 2, indicates a structure featuring a mononuclear zirconium chelate having a pseudo trigonal bi-pyrimidal (TBP) geometry, with axial 0 atoms and equatorial N, C, C atoms. The two benzylic carbon atoms, the nitrogen atom and the metal atom, all lie in the same plane, as the sum of the (CH$_2$)$^1$—Zr—(CH$_2$)$^2$ angle (117.39°), the (CH$_2$)$^1$—Zr—N angle (114.45°) and the (CH$_2$)$^2$—Zr—N angle (128.15°) equals 360.0°. The acute Zr—(CH$_2$)—C(Ar) angle (89.4°), as well as the short Zr—C(Ar) distance (2.71 Å), for one of the benzyl groups, indicate that the pi-system of the benzyl ligand interacts with the metal center, namely, there is a non classical η$^2$ binding of this group to the Zr atom, as taught by Cloke, F. G. N. et al., in *J. Organomet. Chem.* 506, 343, 1996.

EXAMPLE 6

Synthesis of Amine Bis(phenolate) Ligand-metal Chelate Pre-catalyst [2-Pyridine-CH$_2$—]—Zr(CH$_2$Ph)$_2$ 13

As another example of a specific form of general amine bis(phenolate) ligand-metal chelate pre-catalyst 1, the six coordinate dialkyl amine bis(phenolate) ligand-metal chelate pre-catalyst, [2-Pyridine-CH$_2$—]—Zr(CH$_2$Ph)$_2$ 13, was synthesized.

A solution of amine bis(2-hydroxyarylmethyl) ligand precursor [2-Pyridine-CH$_2$—] 12, synthesized according to Example 3, (150 mg, 0.28 mmol) in toluene (5 mL), was added dropwise to a solution of zirconium tetra(benzyl) (0.28 mmol) in toluene (5 mL), at room temperature under nitrogen gas inert atmosphere. The reaction mixture was then heated to 65° C. and stirred for two hours. The toluene was removed from the reaction mixture under low pressure to yield pre-catalyst 13, 99% pure, as a yellow solid.

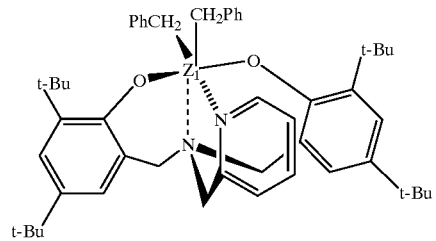

13

Spectroscopic Data of 13. $^1$H NMR (C$_6$D$_6$, 200 MHz) δ8.17 (d, J=5.2, 1H), 7.83 (d, J=7.6, 2H), 7.40 (t, J=7.6, 2H), 7.35 (d, J=2.3, 2H), 7.06 (m, 3H), 6.89 (t, J=7.3, 2H), 6.81 (d, J=2.3, 2H), 6.65 (t, J=7.2, 1H), 6.33 (t, J=7.5, 1H), 6.10 (t, J=6.1, 1H), 5.59 (d, J=7.7, 1H), 3.77 (d, J=13.1, 2H, CH$_2$), 3.23 (s, 2H, CH$_2$), 2.92 (s, 2H, CH$_2$), 2.63 (d, J=13.1, 2H, CH$_2$), 2.59 (s, 2H, CH$_2$), 2.06 (m, 2H, CH$_2$), 1.70 (s, 18H, CH$_3$), 1.34 (s, 18H, CH$_3$).

The spectroscopic data of 13 are consistent with a single stereoisomer featuring symmetrically related phenolate rings, two different benzyl groups, and an AX spin system for the two benzylic methylene groups. This points to another rigid chelate of C$_s$ symmetry on the NMR time scale, with the benzyl groups in a cis geometry, as required for alpha-olefin polymerization catalysts, and the phenolate groups in a trans geometry.

EXAMPLE 7

Polymerization of 1-hexene, in Neat 1-hexene, Using Amine Bis(phenolate) Ligand-metal Chelate Pre-catalyst [(CH$_3$)$_2$N—CH$_2$—CH$_2$—]—Zr(CH$_2$Ph)$_2$ 9

A solution of co-catalyst B(C$_6$F$_5$)$_3$ (0.01 mmol) in 1-hexene (5 mL), was added dropwise to a solution of pre-catalyst 9 (10 mg, 0.01 mmol) in 1-hexene (5 mL), at room temperature under nitrogen atmosphere. The reaction mixture was stirred for a couple of minutes, during which substantial heat was evolved, causing boiling of the 1-hexene, and reaction mixture color changed from yellow to colorless, and back to yellow. The small quantity of remaining 1-hexene monomer reactant/solvent was removed under low pressure to yield poly(1-hexene), 95%, as a colorless sticky oil.

Catalytic activity calculated from reaction data: 15,500 (grams poly(1-hexene) produced)/(mmole-pre-cat. hr).

Molecular weight obtained: M$_w$=12,700 grams/mole, with a PDI of 6.

Spectroscopic data of the poly(1-hexene) product. $^1$H NMR (CDCl$_3$, 200 MHz) δ1.23 (bs, 8H, CH$_2$), 1.06 (bs, 1H, CH), 0.89 (t, J=5.6, 3H, CH$_3$). $^{13}$C NMR (CDCl$_3$, 50.38 MHz) δ40.95 (br, CH$_2$), 35.04 (br, CH$_2$), 32.99 (CH), 29.39 (CH$_2$), 29.03 (CH$_2$), 24.01 (CH$_2$), 14.94 (CH$_3$).

EXAMPLE 8

Polymenzation of 1-hexene, in dilute 1-hexene, Using Amine Bis(phenolate) Ligand-metal Chelate Pre-catalyst [(CH$_3$)$_2$N—CH$_2$—CH$_2$—]—Zr(CH$_2$Ph)$_2$ 9

A solution of co-catalyst B(C$_6$F$_5$)$_3$ (0.005 mmol) in 1-hexene (1 mL) and heptane (1 mL), was added drop-wise to a solution of pre-catalyst 9 (5 mg, 0.005 mmol) in 1-hexene (2 mL) and heptane (6 mL), at room temperature under nitrogen atmosphere. In each instance of dissolving pre-catalyst and co-catalyst, heptane was used as an inert diluent of 1-hexene reactant/solvent, leading to an initial reaction mixture heptane:1-hexene volume ratio of 7:3. The reaction mixture was stirred for 8 minutes, during which evolution of heat was relatively mild compared to heat evolution during the polymerization reaction described in Example 7. Reaction mixture color changed from yellow to colorless. Remaining quantities of 1-hexene monomer reactant/solvent and of heptane diluent were removed under low pressure to yield poly(1-hexene), 85%, as a colorless sticky oil.

Catalytic activity calculated from reaction data: 2000 (grams poly(1-hexene) produced)/(mmole-pre-cat. hr). Time dependence of the consumption of 1-hexene monomer using pre-catalyst 9 activated in dilute 1-hexene solvent is shown in FIG. 3. Molecular weight obtained: $M_w$=170,000 grams/mole, with a PDI of 2.2.

EXAMPLE 9

Polymerization of 1-hexene, in Neat 1-hexene, Using Amine Bis(phenolate) Ligand-metal Chelate Pre-catalyst [$CH_3$—$CH_2$—$CH_2$—]—$Zr(CH_2Ph)_2$ 11

A solution of co-catalyst $B(C_6F_5)_3$ (0.01 mmol) in 1-hexene (1 mL), was added drop-wise to a solution of pre-catalyst 11 (10 mg, 0.01 mmol) in 1-hexene (1mL), at room temperature under nitrogen atmosphere. The reaction mixture was stirred for a couple of minutes. The remaining 1-hexene monomer reactant/solvent was removed under low pressure to yield oligo(1-hexene) of about 20 monomers per chain, as a colorless sticky oil.

Catalytic activity calculated from reaction data: 23 (grams poly(1-hexene) produced)/(mmole-pre-cat. hr).

EXAMPLE 10

Polymerization of 1-hexene, in Neat 1-hexene, Using Amine Bis(phenolate) Ligand-metal Chelate Pre-catalyst [2-Pyridine-$CH_2$—]—$Zr(CH_2Ph)_2$ 13

A solution of co-catalyst $B(C_6F_5)_3$ (0.01 mmol) in 1-hexene (1 mL), was added dropwise to a solution of pre-catalyst 13 (10 mg, 0.01 mmol) in 1-hexene (1 mL), at room temperature under nitrogen atmosphere. The reaction mixture was stirred for a couple of minutes, during which substantial heat was evolved, causing boiling of the 1-hexene, and reaction mixture color changed from yellow to colorless, and back to yellow. The 1-hexene monomer was boiled and reaction mixture color changed from yellow to colorless, and back to yellow. The small quantity of remaining 1-hexene monomer reactant/solvent was removed under low pressure to yield poly(1-hexene), 95%, as a colorless sticky oil.

Catalytic activity calculated from reaction data: about 10,000 (grams poly(1-hexene) produced)/(mmole-pre-cat. hr).

While the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A compound having a general structure selected from the group consisting of:

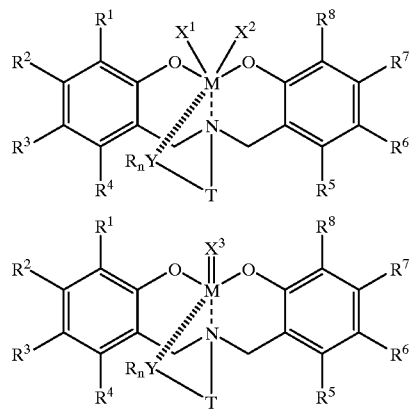

wherein:
a solid line represents a covalent bond;
a dashed line represents a bond having a varying degree of covalency and a varying degree of coordination;
M is a metal atom covalently bonded to each O atom and bonded with varying degrees of covalency and coordination to said N atom;
$X^1$ and $X^2$ are each a univalent anionic ligand covalently bonded to said metal atom;
$X^3$ is a single divalent anionic ligand covalently bonded to said metal atom;
$R^1$ through $R^4$ are each a univalent radical covalently bonded to first ($C_6$) aromatic group;
$R^5$ through $R^8$ are each a univalent radical covalently bonded to second ($C_6$) aromatic group; and
($R_nY$—T) is an optional group selected from the group consisting of a non-donor group covalently bonded to said N atom, wherein said non-donor group, T is a covalent bridging group between said N atom and Y, said Y is a group covalently bonded to said T, and, each of at least one $R_n$ is selected from the group consisting of a saturated substituent covalently bonded to said Y, an unsaturated substituent covalently bonded to said Y, and a univalent radical covalently bonded to said Y, and a donor group covalently bonded to said N atom, wherein said donor group, T is a covalent bridging group between said N atom and Y, said Y is a heteroatom covalently bonded to said T and bonded with varying degrees of covalency and coordination to said metal atom, and, optional $R_n$ substituents are selected from the group consisting of at least one saturated substituent covalently bonded to said Y, and at least one unsaturated substituent covalently bonded to said Y.

2. The compound of claim 1, wherein said metal atom is a transition metal atom.

3. The compound of claim 2, wherein said transition metal atom is selected from the group consisting of zirconium, hafnium and titanium.

4. The compound of claim 1, wherein said $X^1$ and said $X^2$ are each selected from the group consisting of a halide, a hydride, a saturated hydrocarbyl, an unsaturated hydrocarbyl, an alkoxide, an aryloxide, an dialkylamide, and an arylamide.

5. The compound of claim 1, wherein said $X^3$ is selected from the group consisting of a cyclometallated hydrocarbyl, and a radical, said radical including an alkylidene.

6. The compound of claim 1, wherein each of said $R^1$ through $R^4$ is selected from the group consisting of a hydrogen radical, a hydrocarbyl radical, and an alkoxide radical.

7. The compound of claim 1, wherein each of said $R^5$ through $R^8$ is selected from the group consisting of a hydrogen radical, a hydrocarbyl radical, and an alkoxide radical.

8. The compound of claim 1, including said $(R_nY—T)$ group as a said non-donor group, wherein said T is a said covalent bridging group selected from the group consisting of a saturated hydrocarbyl, and an unsaturated hydrocarbyl.

9. The compound of claim 1, including said $(R_nY—T)$ group as a said non-donor group, wherein said Y is selected from the group consisting of a saturated hydrocarbyl, and an unsaturated hydrocarbyl.

10. The compound of claim 1, including said $(R_nY—T)$ group as a said non-donor group, wherein said each of at least one $R_n$ is a said saturated substituent selected from the group consisting of a methyl substituent and an ethyl substituent.

11. The compound of claim 1, including said $(R_nY—T)$ group as a said non-donor group, wherein said each of at least one $R_n$ is a said univalent radical selected from the group consisting of a hydrogen radical and a methyl radical.

12. The compound of claim 1, including said $(R_nY—T)$ group as a said donor group, wherein said T is a said covalent bridging group selected from the group consisting of a saturated hydrocarbyl, an unsaturated hydrocarbyl, and a part of an aromatic system.

13. The compound of claim 12, wherein said saturated hydrocarbyl is selected from the group consisting of a methyl group and an ethyl group.

14. The compound of claim 12, wherein said unsaturated hydrocarbyl is an ethylene group.

15. The compound of claim 12, wherein said aromatic system is a pyridine ring.

16. The compound of claim 1, including said $(R_nY—T)$ group as a said donor group, wherein said Y is a said heteroatom selected from the group consisting of nitrogen, oxygen, sulfur, and phosphorous.

17. The compound of claim 1, including said $(R_nY—T)$ group as a said donor group, wherein said optional $R_n$ substituents are said at least one said saturated substituent selected from the group consisting of a methyl substituent and an ethyl substituent.

18. The compound of claim 1, including said $(R_nY—T)$ group as a said donor group, wherein said optional $R_n$ substituents are said at least one said unsaturated substituent, said unsaturated substituent includes a part of an aromatic system.

19. A compound of a general formula selected from the group consisting of:

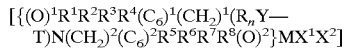

and

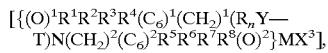

wherein:

M is a metal atom covalently bonded to each said $(O)^1$ atom and bonded with varying degrees of covalency and coordination to said N atom;

$X^1$ and $X^2$ are each a univalent anionic ligand covalently bonded to said metal atom;

$X^3$ is a single divalent anionic ligand covalently bonded to said metal atom;

$(C_6)^1$ is a six carbon aromatic group covalently bonded to $(O)^1$ and covalently bonded to $(CH_2)^1$;

$R^1$ through $R^4$ are each a univalent radical covalently bonded to said $(C_6)^1$ group;

$(C_6)^2$ is a six carbon aromatic group covalently bonded to $(O)^2$ and covalently bonded to $(CH_2)^2$;

$R^5$ through $R^8$ are each a univalent radical covalently bonded to said $(C_6)^2$ group; and $(R_nY—T)$ is an optional group selected from the group consisting of a non-donor group covalently bonded to said N atom, wherein said non-donor group, T is a covalent bridging group between said N atom and Y, said Y is a group covalently bonded to said T, and, each of at least one $R_n$ is selected from the group consisting of a saturated substituent covalently bonded to said Y, an unsaturated substituent covalently bonded to said Y, and a univalent radical covalently bonded to said Y, and a donor group covalently bonded to said N atom, wherein said donor group, T is a covalent bridging group between said N atom and Y, said Y is a heteroatom covalently bonded to said T and bonded with varying degrees of covalency and coordination to said metal atom, and, optional $R_n$ substituents are selected from the group consisting of at least one saturated substituent covalently bonded to said Y, and at least one unsaturated substituent covalently bonded to said Y.

20. The compound of claim 19, wherein said metal atom is a transition metal atom.

21. The compound of claim 19, wherein said transition metal atom is selected from the group consisting of zirconium, hafnium and titanium.

22. The compound of claim 19, wherein said $X^1$ and said $X^2$ are each selected from the group consisting of a halide, a hydride, a saturated hydrocarbyl, an unsaturated hydrocarbyl, an alkoxide, an aryloxide, an dialkylamide, and an arylamide.

23. The compound of claim 19, wherein said $X^3$ is selected from the group consisting of a cyclometallated hydrocarbyl, and a radical, said radical including an alkylidene.

24. The compound of claim 19, wherein each of said $R^1$ through $R^4$ is selected from the group consisting of a hydrogen radical, a hydrocarbyl radical, and an alkoxide radical.

25. The compound of claim 19, wherein each of said $R^5$ through $R^8$ is selected from the group consisting of a hydrogen radical, a hydrocarbyl radical, and an alkoxide radical.

26. The compound of claim 19, including said $(R_nY—T)$ group as a said non-donor group, wherein said T is a said covalent bridging group selected from the group consisting of a saturated hydrocarbyl, and an unsaturated hydrocarbyl.

27. The compound of claim 19, including said $(R_nY—T)$ group as a said non-donor group, wherein said Y is selected from the group consisting of a saturated hydrocarbyl, and an unsaturated hydrocarbyl.

28. The compound of claim 19, including said $(R_nY—T)$ group as a said non-donor group, wherein said each of at least one $R_n$ is a said saturated substituent selected from the group consisting of a methyl substituent and an ethyl substituent.

29. The compound of claim 19, including said $(R_nY—T)$ group as a said non-donor group, wherein said each of at least one $R_n$ is a said univalent radical selected from the group consisting of a hydrogen radical and a methyl radical.

30. The compound of claim 19, including said $(R_nY—T)$ group, said $(R_nY—T)$ group is a said donor group, wherein said T is a said covalent bridging group selected from the group consisting of a saturated hydrocarbyl, an unsaturated hydrocarbyl, and a part of an aromatic system.

31. The compound of claim 30, wherein said saturated hydrocarbyl is selected from the group consisting of a methyl group and an ethyl group.

32. The compound of claim 30, wherein said unsaturated hydrocarbyl is an ethylene group.

33. The compound of claim 30, wherein said aromatic system is a pyridine ring.

34. The compound of claim 19, including said ($R_nY$—T) group, said ($R_nY$—T) group is a said donor group, wherein said Y is a said heteroatom selected from the group consisting of nitrogen, oxygen, sulfur, and phosphorous.

35. The compound of claim 19, including said ($R_nY$—T) group, said ($R_nY$—T) group is a said donor group, wherein said optional $R_n$ substituents are said at least one said saturated substituent selected from the group consisting of a methyl substituent and an ethyl substituent.

36. The compound of claim 19, including said ($R_nY$—T) group, said ($R_nY$—T) group is a said donor group, wherein said optional $R_n$ substituents are said at least one said unsaturated substituent, said unsaturated substituent includes a part of an aromatic system.

\* \* \* \* \*

UNITED STATES PATENT AND TRADEMARK OFFICE
CERTIFICATE OF CORRECTION

PATENT NO. : 6,333,423 B1
DATED : December 25, 2001
INVENTOR(S) : Kol et al.

It is certified that error appears in the above-identified patent and that said Letters Patent is hereby corrected as shown below:

Column 18,
Line 48, correct "diallyl" to -- dialkyl --

Column 21,
Line 5, correct "olmerization" to -- polymerization --
Line 34, correct "pectroscopy" to -- spectroscopy --

Column 22,
Line 24, correct "olmerization" to -- polymerization --
Line 25, correct "valved" to -- evolved --

Column 24,
Line 5, correct "vailable" to -- available --

Column 27,
Line 36, correct "0 (zero)" to -- O (the letter) --

Signed and Sealed this

Fourth Day of June, 2002

*Attest:*

*Attesting Officer*

JAMES E. ROGAN
*Director of the United States Patent and Trademark Office*